(12) United States Patent
Vogt et al.

(10) Patent No.: US 12,408,964 B2
(45) Date of Patent: Sep. 9, 2025

(54) DEVICE AND METHOD FOR PROVIDING A BONE CEMENT PASTE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 207 days.

(21) Appl. No.: 18/351,937

(22) Filed: Jul. 13, 2023

(65) Prior Publication Data

US 2024/0024006 A1    Jan. 25, 2024

(30) Foreign Application Priority Data

Jul. 19, 2022    (EP) .................................... 22185605

(51) Int. Cl.
*A61B 17/88*    (2006.01)

(52) U.S. Cl.
CPC ...... *A61B 17/8833* (2013.01); *A61B 17/8822* (2013.01); *A61B 2017/8838* (2013.01)

(58) Field of Classification Search
CPC ............ A61B 17/8802; A61B 17/8822; A61B 17/8833; A61B 2017/8838
See application file for complete search history.

(56) References Cited

U.S. PATENT DOCUMENTS

| 4,671,263 A | 6/1987 | Draenert |
|---|---|---|
| 4,973,168 A | 11/1990 | Chan |
| 5,100,241 A | 3/1992 | Chan |
| 5,344,232 A | 9/1994 | Nelson et al. |
| 5,586,821 A | 12/1996 | Bonitati et al. |
| 5,588,745 A | 12/1996 | Tanaka et al. |
| 5,624,184 A | 4/1997 | Chan |
| 5,997,544 A | 12/1999 | Nies et al. |
| 6,033,105 A | 3/2000 | Barker et al. |
| 6,709,149 B1 | 3/2004 | Tepic |

(Continued)

FOREIGN PATENT DOCUMENTS

| DE | 3640279 A1 | 6/1987 |
|---|---|---|
| DE | 69812726 T2 | 2/2004 |

(Continued)

*Primary Examiner* — Si Ming Ku

(74) *Attorney, Agent, or Firm* — Dicke, Billig & Czaja, PLLC

(57) ABSTRACT

A device for providing a bone cement paste from two starting components, comprising a mixing unit comprising a hollow cylindrical cartridge with an interior space, wherein a discharge piston axially movable in the interior space is arranged in the space, which piston divides the interior space into a proximal part of the interior space and a distal part of the interior space, wherein the proximal part and the distal part of the interior space are connected to one another in a fluid-conducting manner via a conduit means, wherein a bone cement powder is stored in the proximal part of the interior space as the first starting component, and wherein a conveying piston axially movable in the interior space is arranged in the distal part of the interior space, and a reservoir for a monomer liquid as a second starting component, which is connected or connectable in a fluid-conducting manner.

15 Claims, 13 Drawing Sheets

(56) References Cited

U.S. PATENT DOCUMENTS

| | | |
|---|---|---|
| 2003/0067837 A1 | 4/2003 | Seaton et al. |
| 2017/0354939 A1* | 12/2017 | Vogt .................... B01F 27/2122 |
| 2018/0132917 A1* | 5/2018 | Vogt ................. B01F 33/50112 |

FOREIGN PATENT DOCUMENTS

| | | |
|---|---|---|
| DE | 102009031178 B3 | 9/2010 |
| DE | 102018131266 A1 | 6/2020 |
| EP | 0796653 A2 | 9/1997 |
| EP | 0692229 B1 | 12/1999 |
| EP | 1005901 A2 | 6/2000 |
| EP | 1016452 A2 | 7/2000 |
| EP | 1020167 A2 | 7/2000 |
| EP | 1140234 B1 | 3/2003 |
| EP | 1886647 A1 | 2/2008 |
| EP | 3100694 A1 | 12/2016 |
| EP | 3320870 B1 | 7/2019 |
| EP | 3643398 A1 | 4/2020 |
| EP | 3403716 B1 | 3/2021 |
| EP | 3838391 A1 | 6/2021 |
| WO | 9426403 A1 | 11/1994 |
| WO | 9967015 A1 | 12/1999 |

* cited by examiner

DEVICE AND METHOD FOR PROVIDING A BONE CEMENT PASTE

CROSS-REFERENCE TO RELATED APPLICATIONS

This application claims priority pursuant to 35 U.S.C. 119(a) to European Application No. 22185605.7, filed Jul. 19, 2022, which application is incorporated herein by reference in its entirety.

FIELD OF THE INVENTION

The invention relates to a device for providing a bone cement paste from two starting components, comprising
  a mixing unit comprising a hollow cylindrical cartridge with an interior space, wherein a discharge piston axially movable in the interior space is arranged in the interior space, which piston divides the interior space into a proximal part of the interior space and a distal part of the interior space, wherein the proximal part and the distal part of the interior space are connected to one another in a fluid-conducting manner via a conduit means,
  wherein a bone cement powder is stored in the proximal part of the interior space as the first starting component, and wherein a conveying piston axially movable in the interior space is arranged in the distal part of the interior space,
  and a reservoir for a monomer liquid as a second starting component, which is connected or connectable in a fluid-conducting manner via an inlet channel to the distal part of the interior space for introducing the monomer liquid from the reservoir into the mixing unit.

The invention further relates to a method for providing a bone cement paste from two starting components by means of such a device.

BACKGROUND OF THE INVENTION

Considerable efforts are being made to demonstrate devices and methods for providing bone cement by means of which bone cement paste can be provided easily, reliably, and quickly. One important aspect of providing bone cement paste is the avoidance of air inclusions, e.g., gas bubbles, in the bone cement. To avoid this, a plurality of vacuum cementing systems have been described, of which the following are mentioned by way of example: U.S. Pat. No. 6,033,105 A, 5,624,184 A, 4,671,263 A, 4,973,168 A, 5,100,241 A, WO 99/67015 A1, EP 1020167 A2, US 5,586,821 A, EP 1016452 A2, DE 3640279 A1, WO 94/26403 A1, EP 1005901 A2, EP 1886647 A1, and U.S. Pat. No. 5,344,232 A.

Within the market, there is a desire to simplify the provision of bone cement paste. One development consists of developing cementing systems in which both starting components are stored in separate regions of the mixing systems and are only mixed with one another in the cementing system immediately before the cementing application. Such closed, so-called full-prepacked systems are mentioned, for example, in the following publications: EP 0 692 229 A1, DE 10 2009 031 178 B3, U.S. Pat. No. 5,997,544 A, 6,709,149 B1, DE 698 12 726 T2, EP 0 796 653 A2, and US 5,588,745 A.

In the aforementioned full-prepacked systems, the mixing of a monomer liquid with a bone cement powder is carried out by mechanical mixing, for example by means of a mixing rod.

In contrast to the aforementioned full-prepacked systems, the specification EP 3 320 870 B1 describes a device in which the mixing of a monomer liquid with a bone cement powder takes place merely by pressing the monomer liquid into, in particular compacted, bone cement powder. The device described therefore does not require mechanical mixing, in particular a mixing rod. Consequently, such devices are designed without mixing devices.

In the device, a container filled with monomer liquid is stored axially behind a region filled with a bone cement powder inside a cartridge. A discharge piston is arranged between the bone cement powder and the container. In order to provide a bone cement paste, a conveying piston, which is arranged on a side of the container opposite the discharge piston, is driven forward in the direction of the discharge piston, resulting in opening of the container, in particular by partial shattering of a container in the form of a glass ampoule into container parts. The monomer liquid exiting the container is conveyed into the bone cement powder by continued advancement of the conveying piston, forming the bone cement paste.

Comparable devices are also described in the specifications EP 3 320 869 B1 and EP 3 403 716 B1.

A disadvantage of these devices is that in order to open and convey the monomer liquid into the bone cement powder, the container must be substantially completely destroyed, which on the one hand requires a comparatively high effort on the part of a user of the device and on the other hand makes it difficult to convey the monomer liquid into the bone cement powder substantially completely, in particular because of the fragments of the container.

The patent application EP3838391 A1 also describes a device without mixing apparatus for providing bone cement paste.

In this device, a container filled with a monomer liquid is stored in a reservoir, from which the monomer liquid, after opening the container, can flow via a conduit means into a distal part of an interior space before being conveyable by propelling a piston into a bone cement powder in a proximal part of the interior space. In this case, the reservoir is arranged such that the container is neither opened by the piston nor compressed when the monomer liquid is conveyed into the bone cement powder.

A disadvantage of this device is that the monomer liquid can only flow slowly and/or intermittently through the conduit means into the distal part of the interior space, since the diameter of the conduit means must be designed such that the container, or parts thereof, cannot pass through the conduit means into the interior space. Furthermore, it is only with difficulty that a gas displaced from the interior space by the monomer liquid flowing into the interior can be discharged through the conduit means. The conduit means is therefore not designed for good mass transfer between reservoir and interior space. This is a disadvantage, since a fast, safe and substantially complete provision of the monomer liquid for mixing the bone cement paste is required, especially for time-critical operations. A further disadvantage of the device is its rather complex design with many moving parts. In addition, the piston, which has already been used to convey the monomer liquid into the bone cement powder, is not designed to discharge the bone cement paste from the device. In particular, the reservoir protruding from the device would also make it difficult to discharge the bone cement paste from the device for steric reasons.

There is therefore demand in the market for further simplification of devices for providing bone cement paste.

Objects

It is an object of the present invention to at least partially overcome one or more of the disadvantages resulting from the prior art.

The invention is especially based on the goal of providing a device which permits simple and application-safe opening of one or more ampoules, in particular glass ampoules, with a monomer liquid for the simple, rapid, and application-safe providing of a bone cement paste. In particular, the opening of the ampoule or ampoules should take place with as little effort as possible and with avoidance of additional separate tools. Furthermore, the opening of the ampoule with as few components as possible should be enabled. Furthermore, the monomer liquid should be available with as little loss and as quickly as possible for providing the bone cement paste. Conveying the monomer liquid into a bone cement powder to provide the bone cement paste should be feasible with as little force as possible.

The device is to provide the bone cement paste without mechanical mixing of the starting components. The device should be able to provide the bone cement without an externally applied vacuum. The device should be able to be operated with as few steps as possible in order to minimize sources of error by the user.

A further object of the invention is to provide a method with which bone cement can be provided from two starting components, by means of which at least some of the objects already described are achieved at least in part.

Preferred Embodiments of the Invention

The features of the independent claims contribute to at least partially fulfilling at least one of the aforementioned objects. The dependent claims provide preferred embodiments which contribute to at least partially fulfilling at least one of the objects.

A first embodiment of the invention is a device for providing a bone cement paste from two starting components, comprising:
- a mixing unit comprising a hollow cylindrical cartridge with an interior space, wherein a discharge piston axially movable in the interior space is arranged in the interior space, which piston divides the interior space into a proximal part of the interior space and a distal part of the interior space, wherein the proximal part and the distal part of the interior space are connected to one another in a fluid-conducting manner via a conduit means,
- wherein a bone cement powder is stored in the proximal part of the interior space as the first starting component, and wherein a conveying piston axially movable in the interior space is arranged in the distal part of the interior space,
- and a reservoir for a monomer liquid as a second starting component, which is connected or connectable in a fluid-conducting manner via an inlet channel to the distal part of the interior space for introducing the monomer liquid from the reservoir into the mixing unit, characterized in that
- the reservoir and the mixing unit are connected or connectable in a fluid-conducting manner via an outlet channel, in particular an outlet channel disjoint from the inlet channel, via which a gas can be discharged from the interior space into the reservoir, in particular in order to improve, in particular facilitate and/or accelerate, introduction of the monomer liquid into the mixing unit.

In one embodiment of the device, the reservoir comprises a reservoir container in which at least one ampoule, closed in terms of fluid conduction, having an ampoule body and an ampoule head is arranged, and the monomer liquid is stored in the ampoule, and comprises a cavity in the region of the ampoule head,
wherein the cavity is fluid-conductively connected to the inlet channel and comprises a connection to the ampoule, wherein the ampoule head is at least in regions disposed in the connection, and wherein the reservoir container at least in portions comprises a deformable region such that tilting of the ampoule about a pivot point against the connection is enabled. This embodiment is a second embodiment of the invention, which is preferably dependent upon the first embodiment of the invention.

In one embodiment of the device, the inlet channel has a smaller distance to the pivot point than the outlet channel. This embodiment is a third embodiment of the invention, which is preferably dependent upon the second embodiment of the invention.

In one embodiment of the device, the outlet channel opens into the interior space proximal to the inlet channel. This embodiment is a fourth embodiment of the invention which is preferably dependent upon one of the preceding embodiments of the invention.

In one embodiment of the device, the inlet channel is formed as a funnel at an inlet channel end opposite the mixing unit. This embodiment is a fifth embodiment of the invention, which is preferably dependent on one of the preceding embodiments of the invention.

In one embodiment of the device, the outlet channel has a minimum outlet channel diameter which corresponds to at least half the minimum inlet channel diameter of the inlet channel. This embodiment is a sixth embodiment of the invention, which is preferably dependent on one of the preceding embodiments of the invention.

In one embodiment of the device, the inlet channel and the outlet channel are each formed in at least two parts, such that the mixing unit and the reservoir are connected to one another in a fluid-conducting manner in a first channel position of the inlet channel and the outlet channel, and are separated from one another in terms of fluid conduction in a second channel position of the inlet channel and the outlet channel. This embodiment is a seventh embodiment of the invention, which is preferably dependent upon one of the preceding embodiments of the invention.

In one embodiment of the device, the device comprises a closure element which closes or makes closable, in terms of fluid conduction, at least a part of the at least two-part inlet channel and of the at least two-part outlet channel that faces the mixing unit. This embodiment is an eighth embodiment of the invention which is preferably dependent on the seventh embodiment of the invention.

In one embodiment of the device, the mixing unit and the reservoir are reversibly connected or connectable to one another via a first form closure, in particular in the region of the inlet channel and the outlet channel. This embodiment is a ninth embodiment of the invention, which is preferably dependent on the eighth embodiment of the invention.

In one embodiment of the device, the closure element is a rotary valve through which the part of the two-part inlet channel and the two-part outlet channel that faces the mixing unit extends and which, in a first rotary valve position, leaves the inlet channel and the outlet channel in the first channel position and, by rotating to a second rotary valve position, moves the inlet channel and the outlet channel to the second channel position. This embodiment is a tenth embodiment of the invention, which is preferably dependent on the eighth or ninth embodiment of the invention.

In one embodiment of the device, after the reservoir has been separated from the mixing unit by releasing the first form closure, the closure element can be brought into a closure position in order to close, in terms of fluid conduction, the part of the two-part inlet channel and the two-part outlet channel that faces the mixing unit. This embodiment is an eleventh embodiment of the invention, which is preferably dependent on the ninth embodiment of the invention.

In one embodiment of the device, the closure element is a screw. This embodiment is a twelfth embodiment of the device, which is preferably dependent on the eleventh embodiment of the invention.

In one embodiment of the device, the mixing unit and the reservoir are reversibly connected or connectable to one another via a second form closure. This embodiment is a thirteenth embodiment of the invention, which is preferably dependent upon the ninth through twelfth embodiments of the invention.

A fourteenth embodiment of the invention is a method for providing a bone cement paste from two starting components by means of a device in accordance with one of the preceding embodiments of the invention, comprising the steps of:
  a. the monomer liquid flowing from the reservoir through the inlet channel into the distal part of the interior space while simultaneously a gas from the interior space is discharged through the outlet channel into the reservoir,
  b. conveying the monomer liquid from the distal part of the interior space through the conduit means into the proximal part of the interior space by means of advancing the conveying piston in the direction of the discharge piston.

In one embodiment of the method by means of a device according to any of the eighth to thirteenth embodiments of the invention, before the monomer liquid is conveyed in step b., the part of the two-part inlet channel and the two-part outlet channel that faces the mixing unit is closed in terms of fluid conduction by the closure element. This embodiment is a fifteenth embodiment of the invention, which is preferably dependent upon the fourteenth embodiment of the invention.

General

In the present description, range specifications also include the values specified as limits. A specification of the type "in the range of X to Y" with respect to a variable A consequently means that A can assume the values X, Y and values between X and Y. Ranges delimited on one side of the type "up to Y" for a variable A accordingly mean, as a value, Y and less than Y.

Some of the described features are linked to the term "substantially." The term "substantially" is to be understood as meaning that, under real conditions and manufacturing techniques, a mathematically exact interpretation of terms such as "superimposition," "perpendicular," "diameter," or "parallelism" can never be given exactly, but only within certain manufacturing-related error tolerances. For example, "substantially perpendicular axes" enclose an angle of 85 degrees to 95 degrees relative to one another, and "substantially equal volumes" comprise a deviation of up to 5% by volume. An "apparatus consisting substantially of plastic material" comprises, for example, a plastics content of ≥95 to ≤100% by weight. A "substantially complete filling of a volume B" comprises, for example, a filling of ≥95 to ≤100% by volume of the total volume of B.

The terms "proximal" and "distal" are used only to designate the spatially opposite ends of the device or other structural units of the device and do not permit any inference of orientation with respect to a human body, such as a user of the device. "Distally to . . . " and "proximally to . . . " or similar formulations correspondingly express only the spatial arrangement of two structural units of the device in relation to one another.

DETAILED DESCRIPTION

An initial subject of the invention relates to a device for providing a bone cement paste from two starting components, comprising:
  a mixing unit comprising a hollow cylindrical cartridge with an interior space, wherein a discharge piston axially movable in the interior space is arranged in the interior space, which piston divides the interior space into a proximal part of the interior space and a distal part of the interior space, wherein the proximal part and the distal part of the interior space are connected to one another in a fluid-conducting manner via a conduit means,
  wherein a bone cement powder is stored in the proximal part of the interior space as the first starting component, and wherein a conveying piston axially movable in the interior space is arranged in the distal part of the interior space,
  and a reservoir for a monomer liquid as a second starting component, which is connected or connectable in a fluid-conducting manner via an inlet channel to the distal part of the interior space for introducing the monomer liquid from the reservoir into the mixing unit, characterized in that
  the reservoir and the mixing unit are connected or connectable in a fluid-conducting manner via an outlet channel, via which a gas can be discharged from the interior space into the reservoir.

The device is for mixing a bone cement paste of a bone cement powder and a monomer liquid, wherein prior to mixing the bone cement powder is stored in a mixing unit of the device and the monomer liquid can be stored in a reservoir of the device. Preferably, the reservoir stores at least one ampoule, preferably glass ampoule, filled with the monomer liquid. For example, the reservoir stores one or two ampoules, preferably one or two glass ampoules.

The mixing unit is used for mixing the bone cement paste from the bone cement powder and the monomer liquid after conveying the monomer liquid into the mixing unit, in particular after conveying the monomer liquid into an interior space of the mixing unit.

The mixing unit comprises a hollow cylindrical cartridge. A hollow cylindrical cartridge is to be understood as a tubular receptacle which comprises an interior space and a cartridge wall surrounding the interior space. The cross-section of the cartridge can assume any shape. Because the device is easy to manufacture and safe to use, the cross-section, and preferably also the cross-section of the interior space, is of circular design. This allows easy handling for the user and reduces a risk of movable parts wedging within the device, due to the absence of edges. According to the invention, the cartridge can consist of a wide variety of materials or material combinations. For example, the device can consist of a polymer. The polymer is preferably a transparent polymer, since this allows the user to visually check proper functioning of the device during use.

A discharge piston is arranged in the interior space of the cartridges, which is axially movable in the interior space and divides the interior space into a proximal part of the interior space and a distal part of the interior space. The bone cement powder is stored in the proximal part of the interior space, i.e., proximal to the discharge piston. Preferably, the discharge piston is equipped such that and cooperates with the cartridge wall such that substantially the bone cement powder cannot get into the distal part of the interior space.

The discharge piston is further used to discharge the provided bone cement paste from the mixing unit. For this purpose, the discharge piston can be moved from its original position in the direction of a discharge opening of the mixing unit. The discharge opening is preferably located on a side of the bone cement powder axially opposite the discharge piston and thus proximal to the discharge piston. In order to remove a gas from the mixing unit, in particular the proximal part of the interior space, in particular before the bone cement paste is formed, it is preferred that the discharge opening is designed to be gas-permeable. For example, the discharge opening may be closed with a gas-conducting closure, such as a plug, which is removable from the discharge opening for discharging the mixed bone cement paste.

The mixing unit comprises a conveying piston that can move axially in the interior space. The conveying piston is located in the distal part of the interior space, i.e., distal to the discharge piston. The conveying piston closes the mixing unit at a distal cartridge end in such that the monomer liquid conveyed from the reservoir into the distal part of the interior space cannot flow out of the cartridge. In an initial position of the device, the conveying piston is arranged in the interior space such that after the monomer liquid has been conveyed, it is stored between the discharge piston and the conveying piston in the distal part of the interior space.

By advancing the conveying piston in the direction of the discharge piston, i.e., advancing in the proximal direction, the monomer liquid stored in the distal part of the interior space can be conveyed into the bone cement powder through a conduit means in the proximal part of the interior space, which connects the proximal part and the distal part of the interior space in a fluid-conducting manner. Fluid-conducting means that the distal part and the proximal part of the interior space are connected in a manner permeable to liquids—in particular, the monomer liquid—and to gases. In order to prevent bone cement powder from the proximal part from entering the distal part of the interior space, the conduit means is preferably equipped with a filter means, in particular a pore disc, for example made of sintered polypropylene particles, of sintered or compressed polyethylene fibers, of cellulose felt or of cardboard, which makes the conduit means impermeable to solids. In one variant of the device, at least one passage is provided in the discharge piston and/or between the discharge piston and the cartridge wall as conduit means through which the distal part and the proximal part of the interior space are connected to one another in a fluid-conducting manner. In this regard, a filter that is impermeable to the bone cement powder and permeable to the monomer liquid and gases, such as a pore disc made of, for example, sintered polypropylene particles, sintered or compressed polyethylene fibers, cellulose felt, or cardboard, may be disposed in or at one or both ends of the at least one passage. In a further variation of the device, the conduit means is one or more conduits arranged on the exterior of the cartridge or in the cartridge wall and connecting the distal part and the proximal part of the interior space. The discharge piston is bypassed in this variant.

One variant of the device is designed such that continued advancement of the conveying piston in the direction of the discharge piston after the monomer liquid has been conveyed from the distal part of the interior space into the proximal part of the interior space causes the discharge piston to be advanced in the direction of the discharge opening of the device. In this manner, the bone cement paste provided by mixing bone cement powder and monomer liquid can be discharged from the device through the discharge opening. This is a simple manner of ensuring that the bone cement paste is expelled from the cartridge with the same drive as is used for conveying the monomer liquid, namely with the unidirectionally driven conveying piston.

In order to prevent unintentional advancement of the discharge piston in the direction of the discharge opening, a detent means can be arranged on the discharge piston such that the discharge piston can detent with the cartridge, in particular with the cartridge wall, wherein this detent cannot be released by the pressure to be applied when conveying the monomer liquid into the proximal part of the interior space, but can be released by a direct pressure of the conveying piston acting on the discharge piston.

The detent means ensures that the monomer liquid can first be pressed into the bone cement powder, wherein the discharge piston maintains its original position relative to the cartridge and the interior space. Only after the monomer liquid has been largely pressed into the bone cement powder, and thus the bone cement paste is present in the proximal part of the interior space of the cartridge, can the bone cement paste then be pressed out of the proximal part of the cartridge with the discharge piston. Thus, the force required to release the detent is greater than the force required to convey the monomer liquid through the conduit means into the proximal part of the interior space.

The reservoir is used to provide the monomer liquid before it provides the bone cement paste by mixing with the bone cement powder in the mixing unit. Preferably, the monomer liquid is stored in the reservoir until a user of the device wishes to provide the bone cement.

To convey the monomer liquid from the reservoir to the distal part of the interior space of the mixing unit, the reservoir and the distal part of the interior space of the mixing unit are connected or connectable to one another via an inlet channel in a fluid-conducting manner. For this purpose, the inlet channel has an inlet channel diameter which allows the monomer liquid to be conveyed from the reservoir into the mixing unit as quickly as possible. For example, the inlet channel diameter, in particular a minimum inlet channel diameter, is in a range of 1 mm to 4 mm.

In order to improve, in particular accelerate, the conveyance of the monomer liquid from the reservoir into the distal part of the interior space, the reservoir and the distal part of the interior space are, in addition to the inlet channel, connected or connectable to one another via an outlet channel, in particular one that is disjoint from the inlet channel, in a fluid-conducting manner.

If the reservoir and the distal part of the interior space are connected to one another in a fluid-conducting manner via the inlet channel and the outlet channel, this permits improved, in particular accelerated, conveyance of the monomer liquid from the reservoir via the inlet channel into the distal part of the interior space of the mixing unit, while at the same time a gas from the distal part of the interior space, which is displaced from the distal part of the interior space by the monomer liquid entering the distal part of the interior space, can be discharged into the reservoir via the outlet channel. The inlet channel and the outlet channel thus synergistically ensure improved mass transfer between the reservoir and the mixing unit.

Conveying of the monomer liquid from the reservoir via the inlet channel into the mixing unit can be triggered, for example, by gravity, by negative pressure in the mixing unit, in particular in the interior space of the cartridge, or a combination thereof, wherein conveying by means of gravity is preferred. Particularly when conveying by means of gravity, the outlet channel improves the introduction of the monomer liquid into the mixing unit, since the gas displaced from the interior space can be discharged into the reservoir.

The reservoir can consist of a wide range of materials or material combinations. Examples, the reservoir may consist of a polymer. Preferably, the polymer is a transparent polymer, as this allows the user to visually monitor proper operation of the reservoir, particularly leakage of monomer liquid from the reservoir, during a use.

The reservoir can be designed differently to provide the monomer liquid. For example, the monomer liquid may comprise a reservoir interior in which the monomer liquid is stored in a free-flowing manner. Preferably, the monomer liquid is stored within the reservoir in one or more separate receptacles, which facilitates handling and filling of the device, in particular the reservoir, and sterile provision of the monomer liquid. For example, the monomer liquid in the reservoir is provided in a container in the form of a bag. A bag is understood to be a non-rigid, largely flexible storage device capable of storing the monomer liquid in a hermetically sealed and sterile manner and capable of being opened by means of the impact of an opening means, for example by piercing, cutting or tearing. The bags can be manufactured, for example, from a multilayer composite film—preferably comprising an EVOH barrier layer. Optionally, the bags can comprise a metal coating, and in particular an aluminum coating.

Preferably, the reservoir stores at least one ampoule, preferably glass ampoule, containing the monomer liquid. For example, two ampoules containing the monomer liquid, preferably glass ampoules, are stored in the reservoir. Ampoules, in particular glass ampoules, are preferred due to good sterilizability and easy and reliable openability by manual application of force.

An embodiment of the device is characterized in that the reservoir comprises a reservoir container in which at least one ampoule, closed in terms of fluid conduction, having an ampoule body and an ampoule head is arranged, and the monomer liquid is stored in the ampoule, and comprises a cavity in the region of the ampoule head, wherein the cavity is connected to the inlet channel in a fluid-conducting manner and comprises a connection to the ampoule, wherein the ampoule head is arranged at least in regions in the connection and the reservoir container comprises, at least in portions, a deformable region such that tilting of the ampoule about a pivot point against the connection is enabled.

In this embodiment, the reservoir comprises a reservoir container for receiving one or more, preferably two, ampoules closed in terms of fluid conduction and filled with the monomer liquid, in particular a glass ampoule or glass ampoules, having an ampoule head and an ampoule body. The reservoir container surrounds the at least one ampoule, in particular at least the ampoule body, so that the ampoule can be stored securely in the reservoir until it is used. The reservoir container can, for example, be present in the form of a hollow cylinder into which the at least one ampoule is inserted, wherein, for improved transport capability of the device, the reservoir container is shaped such, for example by the reservoir container comprising a cover, that the ampoule cannot escape unintentionally from the device, in particular from the reservoir. The reservoir container is preferably shaped such that two ampoules, in particular two ampoules next to one another, can be stored, preferably with substantially parallel longitudinal axes, in the reservoir.

Furthermore, the reservoir serves to open, in terms of fluid conduction, the at least one ampoule. For this purpose, the reservoir comprises a cavity which is connected via a connection to the ampoule arranged in the reservoir container. The ampoule is stored in the reservoir in such a way that the ampoule head points in the direction of the cavity, whereas the ampoule body is arranged at least partially, preferably entirely, in the reservoir container. The connection extends between cavity and reservoir container, and in fact in such a way that the ampoule head is arranged at least in regions in the connection. For this purpose, the connection has a connection diameter which allows the ampoule head to be inserted into the connection at least in portions. In one embodiment, the connection has a connection diameter which allows the ampoule head to be inserted completely into the connection. The connection diameter is preferably smaller than the diameter of the ampoule body so that the latter cannot be inserted into the connection. For example, the connection is designed as a ring or hollow cylinder, and the ampoule head is surrounded at least in regions by this ring or hollow cylinder. The connection has a structural integrity which exceeds a structural integrity of the ampoule, so that the ampoule can break when it is pressed against the connection.

In order to open the ampoule or, given the presence of two or more ampoules, all ampoules, the reservoir container comprises a deformable region at least in portions, in particular adjacent to a transition of the ampoule head to the ampoule body of the ampoule. In one embodiment, the reservoir container is completely deformable. The deformable region allows tilting of the ampoule about a pivot point against the connection. The connection diameter is in this case matched to the ampoule head in such a way that, during tilting, at least the ampoule body end facing away from the ampoule head is tilted about the pivot point while at least the ampoule head end facing away from the ampoule body remains within the connection, so that the ampoule is opened in a fluid-conducting manner by at least partial bursting of the ampoule, in particular in the region of an ampoule neck between ampoule head and ampoule body. The connection in this case serves primarily to fix the ampoule head against a tilting movement of the ampoule about the pivot point. For example, the connection diameter is not more than 10% larger than the diameter of the ampoule head so that a relatively slight tilting of the ampoule already leads to its opening in terms of fluid conduction.

After opening of the at least one ampoule in terms of fluid conduction, the monomer liquid can flow out of the ampoule into the cavity. The cavity is connected to the mixing unit, in particular to the distal part of the interior space of the mixing unit, via the inlet channel in a fluid-conducting manner. Conveying of the monomer liquid from the cavity via the inlet channel into the mixing unit can be triggered, for example, by gravity, by a vacuum in the mixing unit, in particular in the interior space of the cartridge, or a combination thereof, wherein conveying by means of gravity is preferred. Particularly when conveying by means of gravity, the outlet channel improves the introduction of the monomer liquid into the mixing unit.

An embodiment of the device is characterized in that the inlet channel has a smaller distance to the pivot point than the outlet channel. In particular, an inlet channel end opposite the mixing unit and facing the reservoir has a smaller distance, in particular a smaller spatial distance, to the pivot point than an outlet channel end opposite the mixing unit and facing the reservoir.

The at least one ampoule is opened in a fluid-conducting manner when tilted about the pivot point against the connection in the vicinity of the pivot point, in particular in the region of the neck of the ampoule, such that the monomer liquid can flow out of the at least one ampoule into the cavity. If the inlet channel, in particular the inlet channel end opposite the mixing unit, is arranged closer to the pivot point than the outlet channel, in particular the outlet channel end opposite the mixing unit, the monomer liquid, with substantially perpendicular spatial orientation of the device and without further intervention of a user of the device, will flow substantially completely through the inlet channel into the mixing unit, in particular the distal part of the interior space of the mixing unit, while at the same time the outlet channel will remain substantially free of the mixing unit, thus permitting improved discharge of the gas displaced from the interior space. This arrangement of inlet channel and outlet channel relative to one another thus improves mass transfer between mixing unit and reservoir.

The inlet channel and the outlet channel can open into the interior space, in particular the distal part of the interior space, at the same spatial height along a longitudinal axis of the device, in particular the mixing unit. In this embodiment, the inlet channel and the outlet channel open into the distal part of the interior space of the mixing unit in the broadest sense "next to one another".

An embodiment of the device is characterized in that the inlet channel opens into the interior space, in particular into the distal part of the interior space, proximal to the inlet channel. The outlet channel, in particular an outlet channel end facing the mixing unit, is thus closer to the discharge piston than the inlet channel, in particular an inlet channel end facing the mixing unit. Thus, the inlet channel, in particular the inlet channel end facing the mixing unit, opens closer to the conveying piston than the outlet channel, in particular the outlet channel end facing the mixing unit. This reduces the risk of the monomer liquid flowing out of the interior space through the outlet channel directly after flowing into the interior space through the inlet channel, particularly if, as is preferred due to the design of the device being as compact as possible, the inlet channel and the outlet channel open into the distal part of the interior space close to one another. Preferably, the outlet channel and the inlet channel open into the interior space no further than 1 cm from one another.

In order to ensure that the monomer liquid is conveyed from the reservoir, preferably from the at least one ampoule opened in a fluid-conducting manner stored in the reservoir, substantially completely via the inlet channel, and not via the outlet channel, into the distal part of the interior space, an embodiment of the device is characterized in that the inlet channel is formed as a funnel at the inlet channel end opposite the mixing unit and facing the reservoir. The design as a funnel facilitates the flow of the monomer liquid into the inlet channel. In particular, when storing the monomer liquid in an ampoule, in particular a glass ampoule, the shaping as a funnel can be advantageous, since the monomer liquid may flow out of the at least one ampoule opened in a fluid-conducting manner irregularly, for example intermittently. The design as a funnel improves the reception of the monomer liquid into the inlet channel, in particular in the case of irregular flow. For example, the funnel can assume a diameter in a range of 1 cm to 4 cm. The cross-sectional area of the funnel can be designed round, angular or elliptical, for example.

The implementation as a funnel can take up different proportions of the total length of the inlet channel. For example, the inlet channel can be designed as a funnel over 10% to 95%, preferably 30% to 90%, more preferably 50% to 90%, of the total length of the inlet channel.

The outlet channel and the inlet channel may have different diameters relative to one another.

An embodiment of the device is characterized in that the outlet channel has a minimum outlet channel diameter that is at least half the minimum inlet channel diameter of the inlet channel. The minimum inlet channel diameter is thus preferably at most twice as large as the minimum outlet channel diameter.

This ensures that gas from the interior space can be discharged into the reservoir through the outlet port sufficiently quickly so as not to slow the conveying of the monomer liquid from the reservoir into the interior space.

In a preferred embodiment, the minimum outlet channel diameter and the minimum inlet channel diameter are substantially equal.

The inlet channel and the outlet channel can be designed in one piece. Thus, they can be formed from a single, continuous component.

An embodiment of the device is characterized in that the inlet channel and the outlet channel are formed at least in two parts, preferably in two or three parts, further preferably in two parts, such that the mixing unit, in particular the distal part of the interior space of the mixing unit, and the reservoir, preferably the cavity of the reservoir, are connected to one another in a fluid-conducting manner in a first channel position of the inlet channel and the outlet channel and are separated from one another in terms of fluid conduction in a second channel position of the inlet channel and the outlet channel. Preferably, the inlet channel and the outlet channel are reversible to the first channel position and the second channel position. A one-piece channel cannot reversibly assume two channel positions.

In this embodiment, at least two components, preferably two or three components, more preferably two components, are involved in forming the inlet channel and the outlet channel, and the inlet channel and the outlet channel extend through these components. For example, the inlet channel is formed by connecting two disjoint tubes in a fluid-conducting manner.

Preferably, the part of the channels that faces the mixing unit extends in one of the components and the part of the channels that faces the reservoir extends in another component.

Preferably, the inlet channel and the outlet channel are formed by the same components.

Due to the at least two-part design of inlet channel and outlet channel, both channels can establish a fluid-conducting connection between the reservoir and the mixing unit, preferably reversibly, in a first channel position and separate the reservoir and the mixing unit in a second channel position in a fluid-conducting manner. For example, the inlet channel is formed by connecting two previously disjoint tubes in a fluid-conducting manner, wherein the tubes connected to one another in a fluid-conducting manner represent the first channel position and the two disjoint tubes represent the second channel position.

The at least two-part design of the inlet channel and the outlet channel thus allows a user of the device to control the mass transfer between the mixing unit and the reservoir.

Preferably, the inlet channel and the outlet channel can be moved to the first or second channel position simultaneously.

An embodiment of the device is characterized in that the device comprises a closure element which closes or makes closable in terms of fluid conduction, preferably reversibly closes or makes closable in terms of fluid conduction, at least a part of the at least two-part inlet channel that faces the mixing unit, i.e., adjacent to the mixing unit, and of the a part of the at least two-part outlet channel that faces the mixing unit, i.e., adjacent to the mixing unit. For example, the device comprises a plug reversibly insertable into the inlet channel end and outlet channel end facing the mixing unit to separate the mixing unit and the reservoir in terms of fluid conduction.

The closure element facilitates substantially complete conveying of the monomer liquid from the distal part of the interior space through the conduit means into the proximal part of the interior space. Without the closure element, the monomer liquid, or portions thereof, could be discharged back out of the mixing unit as it is conveyed into the proximal part of the interior space through the inlet channel and/or the outlet channel.

An embodiment of the device is characterized in that the mixing unit and the reservoir are reversibly connected or connectable to one another via a first form closure. Thus, the mixing unit and the reservoir are designed to be reversibly separable from one another, which simplifies the use of the device for a user. This allows easy separation of the reservoir, which is no longer required after the monomer liquid has been conveyed into the mixing unit, in particular into the distal part of the interior space of the mixing unit, thus simplifying the provision, and preferably the discharge, of the bone cement paste by means of the mixing unit, in particular by improving manageability.

Preferably, the same components that form the at least two-part inlet channel and the at least two-part outlet channel are involved in the formation of the first form closure.

In an embodiment, the inlet channel and the outlet channel are in the first channel position when the first form closure is formed and in the second channel position when the first form closure is released.

The closure element can be shaped differently to separate the mixing unit and the reservoir in terms of fluid conduction.

An embodiment of the device is characterized in that the closure element is a rotary valve through which the part of the two-part inlet channel and the two-part outlet channel that faces the mixing unit, i.e. the part of the two-part inlet channel and the two-part outlet channel adjacent to the mixing unit, extends and which, in a first rotary valve position, leaves the inlet channel and the outlet channel in the first channel position and, by rotating to a second rotary valve position, moves the inlet channel and the outlet channel to the second channel position. The part of the at least two-part inlet channel and two-part outlet channel facing away from the mixing unit and toward the reservoir does not extend through the rotary valve in each case. The rotary valve thus forms the component of the at least two-part inlet channel and outlet channel which forms the parts of the two channels that face the mixing unit. When the rotary valve is in the first rotary valve position, the inlet channel and the outlet channel are in the first channel position, thereby connecting the mixing unit, in particular the distal part of the interior space of the mixing unit, and the reservoir in a fluid-conducting manner. When the rotary valve is in the second rotary valve position, the inlet channel and the outlet channel are in the second channel position, thereby separating the mixing unit, in particular the distal part of the interior space of the mixing unit, and the reservoir in terms of fluid conduction. By rotating the rotary valve to the second rotary valve position, and thus moving the inlet channel and the outlet channel to the second channel position, the two parts of the inlet channel and the two parts of the outlet channel are spatially displaced relative to one another such that mass transfer between the respective parts of the inlet channel and the outlet channel is prevented. By rotating the rotary valve to the first rotary valve position, and thus moving the inlet channel and the outlet channel to the first channel position, the two parts of the inlet channel and the two parts of the outlet channel are arranged relative to one another in such a manner as to allow mass transfer between the corresponding parts of the inlet channel and the outlet channel.

An embodiment of the device is characterized in that, after the reservoir has been separated from the mixing unit by releasing the first form closure, the closure element can be brought into a closure position in order to close, in terms of fluid conduction, the part of the two-part inlet channel and the two-part outlet channel that faces the mixing unit. In this embodiment, the parts of the at least two-part inlet channel and the two-part outlet channel are separated in terms of fluid conduction by releasing the first form closure, wherein preferably in each case the part of the inlet channel and of the outlet channel that faces the reservoir, i.e., adjacent to the reservoir, together with the reservoir are removed from the mixing unit by releasing the first form closure, and the parts of the inlet channel and of the outlet channel adjacent to the mixing unit remain on the mixing unit, for example as feedthroughs in the cartridge wall in the region of the distal part of the interior space. In this embodiment, releasing the first form closure moves the inlet channel and the outlet channel from the first channel position to the second channel position. The closure element is used to close the parts of the inlet channel and the outlet channel remaining on the mixing unit, preferably from outside the mixing unit, after the reservoir has been removed. For this purpose, the closure element is brought into the closure position. For example, the closure element is a plug which can be brought into the closure position by pushing it into the part of the inlet channel and outlet channel remaining on the mixing unit, preferably from outside the mixing unit.

An embodiment of the device is characterized in that the closure element is a screw. The screw preferably comprises an external thread which cooperates with an internal thread, which is preferably located outside the mixing unit, such that, after loosening the first form closure and removing the part of the inlet channel and the outlet channel facing the reservoir, screwing in the screw in the direction of the cartridge wall causes fluid-conducting closure of the part of the inlet channel and the outlet channel remaining on the mixing unit, preferably by means of a screw syringe.

Preferably, the screw comprises wings to facilitate screwing to the locking position by a user of the device.

The first form closure may be the only mechanical connection between the mixing unit and the reservoir.

An embodiment of the device is characterized in that the mixing unit and the reservoir are reversibly connected or connectable to one another, in addition to the first form closure, via a second form closure.

In this embodiment, the mixing unit and the reservoir are connected to each other by two form closures.

Upon opening the at least one ampoule by tilting about the pivot point against the connection, a sufficiently large force must be exerted on the ampoule in order to overcome the structural integrity of the ampoule. This force is additionally increased given use of more than one ampoule, such as preferably two ampoules, if the latter are to be opened simultaneously, as is preferred, by tilting about the pivot point against the connection. This force acts on the contact points of the reservoir and mixing unit.

If the reservoir and the mixing unit were connected only via the first form closure, the force for opening the at least one ampoule would act completely on this first form closure, such that, since preferably the components which form the at least two-part inlet channel and the at least two-part outlet channel are involved in the first form closure, kinking or even tearing of the inlet channel and/or the outlet channel could occur. This would make it difficult, if not impossible, to convey substantially all of the monomer liquid from the reservoir into the mixing unit, in particular the distal part of the interior space.

The second form closure between the connecting element and the mixing unit ensures a force distribution of the force, required to open the at least one ampoule, onto the two form closures so that the risk of the device being damaged upon opening the at least one ampoule by tilting is reduced.

Via the two form closures, the reservoir is connected stably to the mixing unit in such a way that the at least one ampoule can be opened by tilting about the pivot point against the connection without damaging the device, and without requiring additional aids in addition to the device to open the at least one ampoule.

The second form closure between the mixing unit and the reservoir can be realized in different ways.

In an embodiment of the device, the second form closure is formed by means of a clasp. Preferably, the clasp is formed of two clasp indentations on a reservoir outer surface, such as an outer surface of the reservoir container, cavity or joint, and two clasp protrusions on a mixing element outer surface, preferably a cartridge outer surface, wherein the two clasp protrusions are reversibly insertable into the two clasp indentations to form the second form closure. This allows a quickly and easily creatable and releasable second form closure, which is stable and allows safe opening of the at least one ampoule by tilting around the pivot point.

The pivot point as well as the first form closure and the second form closure may be arranged spatially in different ways with respect to one another.

One embodiment of the device is characterized in that, in a side view, in particular a side view of the device, the pivot point, the first form closure, and the second form closure form the vertices of a triangle. In this embodiment, the pivot point and the two form closures lie in a common plane but are not arranged on a straight line running in this plane. The longitudinal axis of the cartridge preferably lies within this plane or runs at least parallel to this plane. The arrangement in the form of a triangle improves the force distribution of the force required for the opening of the at least one ampoule in terms of fluid conduction, in particular given a tilting movement, used for this purpose, of the ampoule about the pivot point within or parallel to the plane of the triangle. Furthermore, such an arrangement fixes and does not displace the pivot point in this plane, which facilitates a reproducible opening of the at least one ampoule.

The pivot point as well as the first form closure and the second form closure may have different distances from one another.

One embodiment of the device is characterized in that the second form closure has a shorter distance from the first form closure than the pivot point. In this embodiment, the distance between pivot point and first form closure is thus greater than the distance between second form closure and first form closure. In particular given an arrangement of pivot point and the two form closures in the form of a triangle, this allows both improved force distribution of the force, required during tilting to open the ampoule, onto the two form closures and simultaneously an optimally space-saving design of the device. The latter facilitates in particular the handling of the device by a user.

The pivot point and the two form closures in this case preferably form the vertices of a triangle in a side view, wherein the pivot point and the second form closure have the smallest value of the three possible distances between the mentioned points. This leads to a further improvement of the force distribution onto the two form closures and allows a further space-saving design of the device.

One embodiment of the device is characterized in that the first form closure, the second form closure, and the pivot point respectively lie on a straight line running parallel to a longitudinal axis of the cartridge, wherein the straight lines have a different straight-line distance from the longitudinal axis of the cartridge. This arrangement improves the force distribution of the force, required during tilting to open the ampoule, onto the two form closures and also simultaneously allows an optimally space-saving design of the device. The latter facilitates in particular the handling of the device by a user.

The pivot point and the two form closures in this case preferably form the vertices of a triangle, wherein the triangle lies in a plane in which the longitudinal axis of the cartridge also lies, or to which the longitudinal axis of the cartridge runs at least in parallel.

A further subject matter of the invention relates to a method for providing a bone cement paste from two starting components by means of a device, in particular by means of a device according to any of the preceding embodiments, comprising the following steps:

a. the monomer liquid flowing from the reservoir through the inlet channel into the distal part of the interior space while simultaneously a gas from the interior space is discharged through the outlet channel into the reservoir, b. conveying the monomer liquid from the distal part of the interior space through the conduit means into the proximal part of the interior space by means of advancing the conveying piston in the direction of the discharge piston.

Preferably, the flow of the monomer liquid in step a. occurs in accordance to gravity. For this purpose, the device is held spatially by a user in such a manner that the discharge piston is arranged spatially above the conveying piston, preferably perpendicular above the conveying piston.

As the monomer liquid flows through the inlet channel into the distal part of the interior space, a temporary monomer liquid level may be formed within the inlet channel, which results from an inlet volume of monomer liquid into the inlet channel and an outlet volume of monomer liquid from the inlet channel into the distal part of the interior space. By the aforementioned embodiments of the device, the monomer liquid level is preferably always formed distal to the, reservoir-facing, exit channel end of the exit channel such that when the device is oriented perpendicular with the proximal cartridge end facing upward, substantially no monomer liquid enters the exit channel on the reservoir side.

Driving the conveying piston forward in the direction of the discharge piston in step b. reduces the spatial distance between the two pistons such that, depending on the volume of the monomer liquid present in the distal part of the interior space, at a determined spatial proximity the monomer liquid is conveyed from the distal part of the interior space through the conduit means into the proximal part of the interior space.

With the beginning of conveying the monomer liquid into the proximal part of the interior space, there is a contact of monomer liquid in the bone cement powder stored in the proximal part of the interior space, which is accompanied by formation of the bone cement paste.

An embodiment of the method is characterized in that, before the monomer liquid is conveyed in step b., the part of the two-part inlet channel and the two-part outlet channel that faces the mixing unit is closed in terms of fluid conduction by the closure element.

This facilitates substantially complete conveying of the monomer liquid from the distal part of the interior space through the conduit means into the proximal part of the interior space without substantial portions of the monomer liquid being discharged from the mixing unit from the distal part of the interior space through the inlet channel and/or the outlet channel by advancing the conveying piston. Furthermore, a user does not need to spatially orient the device precisely to substantially eliminate this discharge.

The conveying piston can be advanced in different manners in the direction of the discharge piston. For example, a user of the device can advance the conveying piston manually, in particular by applying force to a rod or axle. In a further embodiment, the cartridge and the conveying piston together form a thread via which the conveying piston can be screwed into the cartridge in the direction of the discharge piston. Preferably, the cartridge comprises an internal thread and the conveying piston comprises an external thread, which interact positively and/or non-positively to enable the conveying piston to be driven forward.

In a further embodiment of the method, the conveying piston is advanced using a mechanical aid.

An embodiment of the method is characterized in that for advancing the conveying piston, the device is inserted into a discharge device, in particular a discharge gun for bone cement paste. Discharge guns for bone cement paste are known to the person skilled in the art.

As the monomer liquid is conveyed from the rear part to the front part of the interior space, the formation of the bone cement paste from the two starting components begins. Preferably, this is carried out by mixing the two starting components as uniformly as possible to obtain a bone cement paste that is as homogeneous as possible. The mixing of the two starting components can be done in different ways. In an embodiment of the method, mixing is carried out with the active participation of the user of the device, for example by shaking the device or by actuating a mixing element in the front part of the interior space, in particular a stirring device.

An embodiment of the method is characterized in that the monomer liquid is distributed in the bone cement powder with the aid of a hydrophilic additive. An advantage is that this takes place without the active participation of the user of the device, which avoids possible errors by the user during mixing. A possible error is that the user does not mix over the entire length of the front part of the interior space, such that parts of the bone cement powder are not wetted with monomer liquid. A further advantage is that the device can thus be designed more simply and with fewer moving parts, which reduces both the risk of malfunctions and the manufacturing costs of the device.

The device is characterized in that it provides a bone cement paste from two starting components. Bone cement paste is understood to mean a substance that is suitable in the field of medical technology for creating a stable connection between artificial joints, such as hip and knee joints, and bone material. By curing, a bone cement paste becomes a bone cement. These bone cements are preferably polymethyl methacrylate bone cements (PMMA bone cements). PMMA bone cements have been used for a long time in medical applications and are based upon the work of Sir Charnley (cf. Charnley, J., Anchorage of the femoral head prosthesis of the shaft of the femur. *J. Bone Joint Surg.* 1960; 42, 28-30.). PMMA bone cements can thereby be produced from a bone cement powder as a first starting component and a monomer liquid as a second starting component. With a suitable composition, the two starting components can be storage-stable, separately from one another. When the two starting components are brought into contact with one another, a plastically-deformable bone cement paste is produced by the swelling of the polymer components of the bone cement powder. In this case, polymerization of the monomer by radicals is initiated. As the polymerization of the monomer progresses, the viscosity of the bone cement paste increases until it cures completely.

Bone cement powder is understood to mean a powder that comprises at least one particulate polymethyl methacrylate and/or a particulate polymethyl methacrylate copolymer. Examples of copolymers are styrene and/or methyl acrylate. In one embodiment, the bone cement powder can additionally comprise a hydrophilic additive which supports the distribution of the monomer liquid within the bone cement powder. In a further embodiment, the bone cement powder can additionally comprise an initiator which initiates the polymerization. In a further embodiment, the bone cement powder can additionally comprise a radiopaque material. In yet another embodiment, the bone cement powder can additionally comprise pharmaceutically-active substances, such as antibiotics.

The bone cement powder preferably comprises, as a hydrophilic additive, at least one particulate polymethyl methacrylate and/or a particulate polymethyl methacrylate copolymer, an initiator, and a radiopaque material, or consists of these components. More preferably, the bone cement powder comprises at least one particulate polymethyl methacrylate and/or a particulate polymethyl methacrylate copolymer, an initiator, a radiopaque material, and a hydrophilic additive, or consists of these components. Most preferably, the bone cement powder comprises at least one particulate polymethyl methacrylate and/or a particulate polymethyl methacrylate copolymer, an initiator, a radiopaque material, a hydrophilic additive, and an antibiotic, or consists of these components.

According to the invention, the particle size of the particulate polymethyl methacrylate and/or of the particulate polymethyl methacrylate copolymer of the bone cement powder can correspond to the sieve fraction of less than 150 µm, preferably less than 100 µm.

According to the invention, the hydrophilic additive can be designed in particulate and/or fibrous form. In a further embodiment, the hydrophilic additive can be slightly soluble, and preferably insoluble, in methyl methacrylate. In a further embodiment, the hydrophilic additive may have an absorption capacity of at least 0.6 g of methyl methacrylate per gram of hydrophilic additive. In a further embodiment, the hydrophilic additive can comprise a chemical substance comprising at least one OH group. In this case, the hydrophilic additive can preferably have covalently-bonded OH groups at its surface. Examples of such preferred hydrophilic additives can be additives selected from the group comprising cellulose, oxycellulose, starch, titanium dioxide, and silicon dioxide, wherein pyrogenic silicon dioxide is particularly preferred. In one embodiment, the particle size of the hydrophilic additive can correspond to the sieve fraction of less than 100 µm, preferably less than 50 µm, and most preferably less than 10 µm. The hydrophilic additive can be contained in an amount of 0.1 to 2.5% by weight, based on the total weight of the bone cement powder.

According to the invention, the initiator can contain dibenzoyl peroxide or consist of dibenzoyl peroxide.

According to the invention, a radiopaque material is understood to mean a substance that makes it possible to make the bone cement visible on diagnostic X-ray images. Examples of radiopaque materials can include barium sulfate, zirconium dioxide, and calcium carbonate.

According to the invention, the pharmaceutically-active substance can comprise one or more antibiotics and, optionally, added cofactors for the one or more antibiotics. Preferably, the pharmaceutically-active substance consists of one or more antibiotics and, optionally, added cofactors for the one or more antibiotics. Examples of antibiotics include, inter alia, gentamicin, clindamycin, and vancomycin.

According to the invention, the monomer liquid can comprise the monomer methyl methacrylate or consist of methyl methacrylate. In one embodiment, the monomer liquid comprises, in addition to the monomer, an activator dissolved therein, such as N,N-dimethyl-p-toluidine, or consists of methyl methacrylate and N,N-dimethyl-p-toluidine.

The features disclosed for the device are also disclosed for the method, and vice versa.

FIGURES

In the following, the invention is illustrated further, by way of example, by figures. The invention is not limited to the figures.

In the figures:

FIG. 1 shows a schematic longitudinal section of an exemplary device for providing a bone cement paste comprising a mixing unit and a reservoir with an ampoule filled with a monomer liquid, FIG. 2 shows the device of FIG. 1, wherein a first form closure, a second form closure, and a pivot point are indicated, FIG. 3 shows a perspective side view of the mixing unit of the device from FIGS. 1 and 2, FIG. 4 shows the device of FIGS. 1 to 3 during a fluid-conducting opening of the ampoule and during conveying of the monomer liquid into the mixing unit, FIG. 5 shows the device of FIGS. 1 to 4, with the reservoir being separate from the mixing unit, FIG. 6 shows the device from FIGS. 1 to 5 with a closure element closed in terms of fluid conduction in the form of a screw, FIG. 7 shows the device of FIGS. 1 to 6 during conveying the monomer liquid into the bone cement powder, FIG. 8 shows the device from FIGS. 1 to 7 with bone cement paste provided, FIG. 9 shows the device from FIGS. 1 to 8 during discharge of the bone cement paste, FIG. 10 shows a schematic longitudinal section of a further exemplary device for providing a bone cement paste comprising a mixing unit and a reservoir with an ampoule filled with a monomer liquid, FIG. 11 shows the device of FIG. 10 during a fluid-conducting opening of the ampoule and during conveying of the monomer liquid into the mixing unit, FIG. 12 shows the device of FIGS. 10 and 11 with a closure element closed in terms of fluid conduction in the form of a rotary valve, and FIG. 13 shows a flow diagram of a method for providing a bone cement paste.

Figure 1:
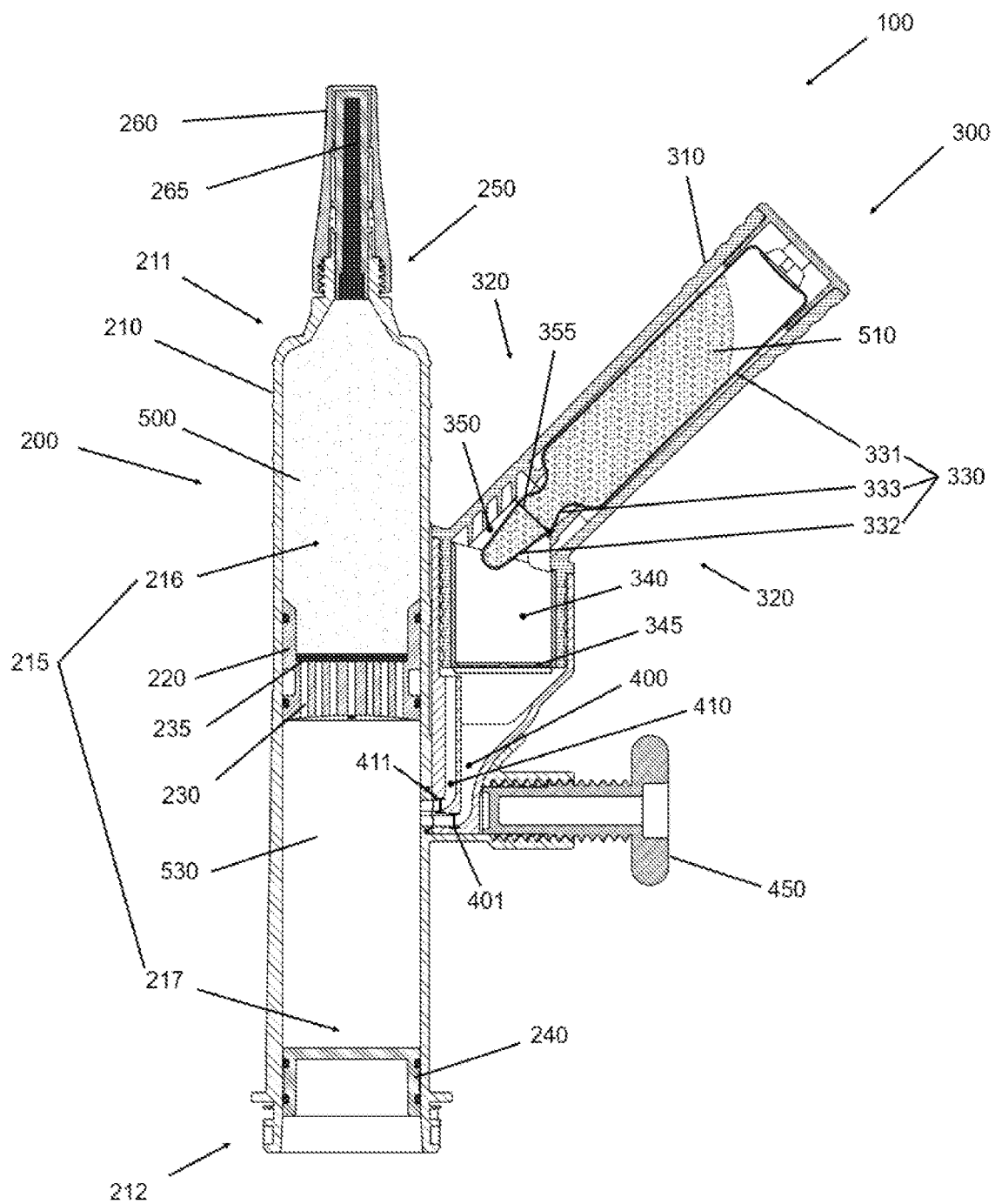
FIG. 1 shows a schematic longitudinal section of an exemplary embodiment of a device 100 for providing a bone cement paste from two starting components in an initial state. The device 100 comprises a mixing unit 200 and a reservoir 300, which are reversibly separably connected to one another via a first form closure and a second form closure (see FIGS. 2 and 3).

The mixing unit 200 is of tubular construction and comprises a hollow cylindrical cartridge 210 having an interior space 215, which is divided into a proximal part 216 and a distal part 217 of the interior space 215 by a discharge piston 220 that is reversibly axially displaceable in the interior space 215. The proximal part 216 of the interior space 215 stores a bone cement powder 500 as a first starting component of the bone cement paste, and the reservoir 300 stores an ampoule 330 containing a monomer liquid 510 as a second starting component of the bone cement paste. The bone cement powder 500 contains particulate polymethyl methacrylate as the main component, as well as a hydrophilic additive that allows the monomer liquid 510 to be dispersed in the bone cement powder 500 without mixing.

The discharge piston 220 is designed to be impermeable to solids such that no bone cement powder 500 can pass from the proximal part 216 into the distal part 216 of the interior space 215. The discharge piston 220 comprises a conduit means 230 (marked only by way of example) in the form of a plurality of passages through which a fluid-conducting connection is formed between the proximal part 216 and the distal part 217 of the interior space 215. The conduit means 230 is impermeably closed to solids or bone cement paste by a filter means 235 in the form of a pore disc, wherein the pore disc allows conveying of the monomer liquid 510 from the distal part 217 into the proximal part 216 of the interior space 215 without any problems. In the embodiment of the device 100 shown, the filter means 235 is disposed on the proximal end of the conduit means 230 facing the proximal part 216 of the interior space 215. In further embodiments, not shown, the filter means 235 is disposed on the distal end of the conduit means 230 facing the distal part 217 of the interior space 215, or on both ends of the conduit means 230. An advantage of a filter means 235 arranged as shown is that the bone cement paste forming in the proximal part 216 of the interior space 215 cannot clog the conduit means 230.

A conveying piston 240 axially movable within the interior space 215 is arranged distal to the discharge piston 220 within the distal part 217 of the interior space 215. The conveying piston 240 closes a distal cartridge end 212 of the cartridge 210 in terms of fluid conduction.

The mixing unit 200 further comprises, at a proximal cartridge end 211 opposite the distal cartridge end 212, a discharge opening 250 that delimits the region of the proximal part 216 of the interior space 215 of the cartridge 210 facing away from the discharge piston 220. In the initial state of the device 100, the discharge opening 250 is closed by a closure cap 260 with a plug 265 such that no bone cement powder 500 can escape from the cartridge 210. The plug 265 is designed to be gas permeable to allow a gas 530 present in the interior space 215 to transfer through the bone cement powder 500 and out of the device 100 before formation of the bone cement paste begins.

The reservoir 300 comprises a tubular reservoir container 310 in which two ampoules 330, in particular two glass ampoules, are stored side by side (only one of the ampoules 330 is visible in the view shown). The ampoules 330 each comprise an ampoule body 331, an ampoule head 332 facing the mixing unit 200, and an ampoule neck 333 located between the ampoule body 331 and the ampoule head 332, which acts as a predetermined breaking point for the ampoules 330. The monomer liquid 510 is stored in the ampoules 330. The ampoule head 332 of the ampoule 330 is arranged in portions in a connection 350 which connects a cavity 340 of the reservoir 300 to the ampoule 330. The connection 350 has a connection diameter 355 that is about 5% larger than a diameter of the ampoule heads 332, such that the connection 350 fixes the ampoule heads 332 against tilting within the drawing plane. To allow tilting of the ampoules 330, in particular the ampoule heads 332, against the connection 350, wherein in the embodiment shown tilting in the drawing plane is possible, the reservoir container 310 comprises a deformable region 320 in the region of a transition from the connection 350 to the ampoule body 331.

Within the cavity 340, a filter element 345 is arranged in the reservoir 300 so that after the ampoules 330 have been opened in terms of fluid conduction, fragments thereof cannot pass via the cavity 340 into the mixing unit 200 but rather are retained on the filter element 345.

The reservoir 300, in particular the cavity 340, is connected to the mixing unit 200, in particular the distal part 217 of the interior space 215, via an inlet channel 400 and an outlet channel 410 in a fluid-conducting manner. In the view shown, the inlet channel 400 and the outlet channel 410 are in a first channel position such that the reservoir 300 and the mixing unit 200 are connected to one another via the two channels 400, 410 in a fluid-conducting manner.

The inlet channel 400 is used to introduce the monomer liquid 510 from the reservoir 300 into the mixing unit. The outlet channel serves to discharge the gas 530 from the mixing unit 200 into the reservoir 300, which is displaced by the monomer liquid 510 flowing into the distal part 217 of the interior space 215. To ensure good mass transfer between the reservoir 300 and the mixing unit 200, the outlet channel 410 in the embodiment shown has a minimum outlet channel diameter 411, which corresponds to a minimum inlet channel diameter 401 of the inlet channel 400. The inlet channel 400 is shaped as a funnel at an end facing the ampoules 330 to better receive the monomer liquid 510 as it flows out of the ampoules 330 to be opened.

Both the inlet channel 400 and the outlet channel 410 are formed in two parts, wherein a part of the inlet channel 400 and of the outlet channel 410 facing the mixing unit 200 is respectively formed as a feedthrough in the cartridge 210, and a part of the inlet channel 400 and of the outlet channel 410 facing the ampoules 330 respectively extends within the reservoir 300 that can be reversibly separated from the mixing unit 200. Thus, the inlet channel 400 and the outlet channel 410 are shaped from two components of the device 100.

Figure 6:
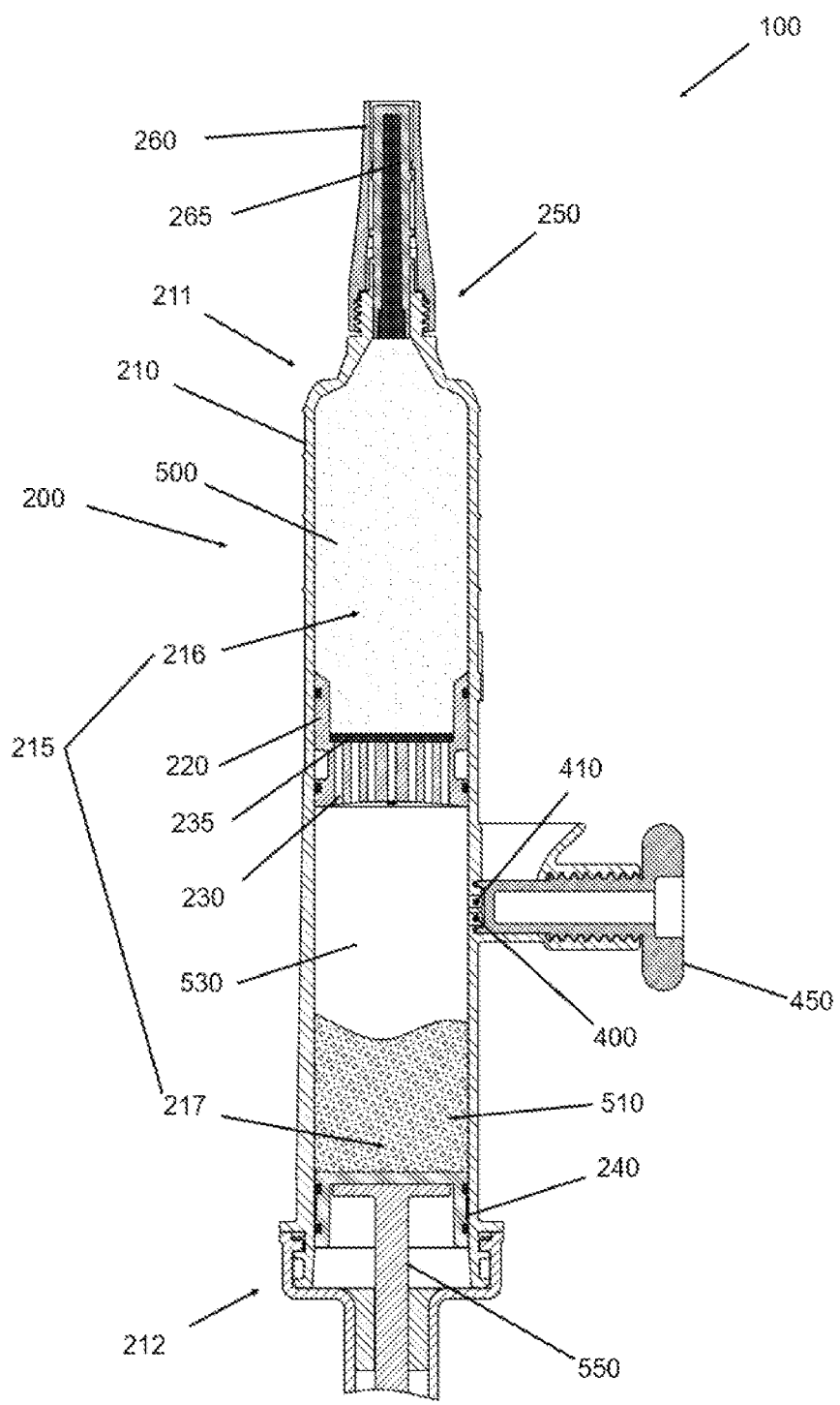

The device 100 further comprises a closure element 450 in the form of a screw which, after separation of the mixing unit 200 and the reservoir 300, can close, in terms of fluid conduction, the parts of the inlet channel 400 and the outlet channel 410 that face the mixing unit 200, i.e., the feedthroughs in the cartridge 210 (cf. FIG. 6).

Figure 2:
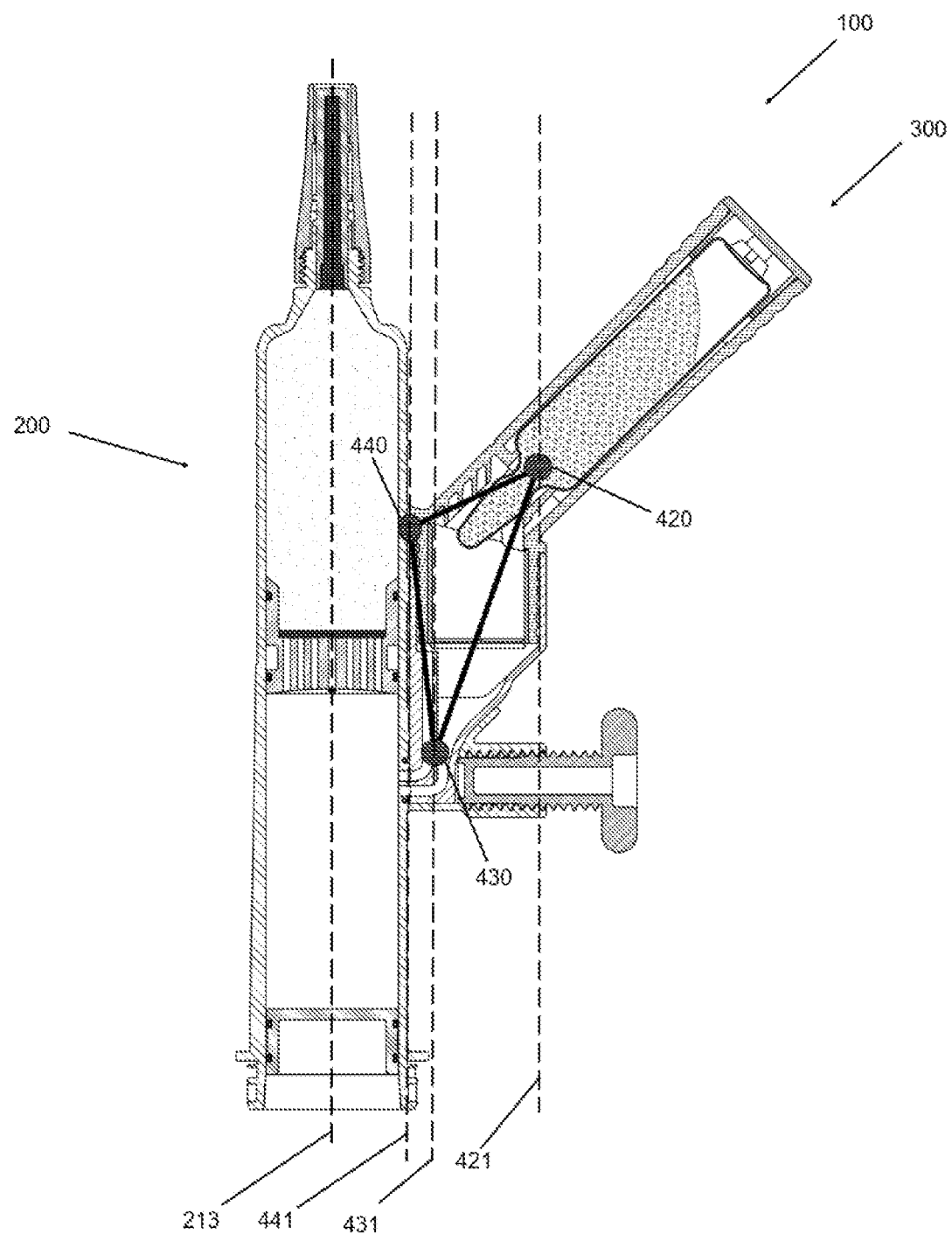

FIG. 2 shows the device 100 of FIG. 1, wherein the first form closure 430, the second form closure 440, and a pivot point 420 about which, due to the deformable region 320, the ampoules 330 can be pressed by tilting against the connection 350 (cf. FIG. 1), are indicated by filled circles.

The first form closure 430 is formed by the components shaping the inlet channel 400 and the outlet channel 410 (cf. FIG. 1) in the region of the inlet channel 400 and the outlet channel 410. The second form closure 430 is designed by a clasp (not shown in FIGS. 1 and 2; cf. FIG. 3).

In the shown side view of the device 100, the first form closure 430, the second form closure 440, and the pivot point 420 form a triangle (indicated by connecting lines between the filled circles). When the ampoules 330 are tilted about the pivot point 420 such that the ampoules 330, in particular the ampoule heads 332 (cf. FIG. 1), are pressed against the connection 350 (cf. FIG. 1), the force required in this case to open the ampoules 330 in a fluid-conducting manner is distributed between the first form closure 430 and the second form closure 440. An advantageous force distribution is achieved via the arrangement of the first form closure 430, the second form closure 440, and the pivot point 420 in the form of a triangle. In particular, this can reduce the risk of kinking or breaking of the inlet channel 400 and outlet channel 410.

The first form closure 430, the second form closure 440, and the pivot point 420 are arranged relative to one another such that the second form closure 440 has a shorter distance from the first form closure 430 than the pivot point 420. The pivot point 420 and the first form closure 430 are thus spaced farther apart from one another than the first form closure 430 and the second form closure 440. This ensures improved force distribution of the force required during tilting about the pivot point 420 to open the ampoules 330 onto the two form closures 430, 440 and also, at the same time, ensures an optimally space-saving design of the device 100. The latter in particular facilitates the handling of the device 100 by a user.

The first form closure 430 lies on a straight line 431 extending parallel to a longitudinal axis 213 of the cartridge 210, the second form closure 440 lies on another straight line 441 extending parallel to the longitudinal axis 213 of the cartridge 210, and the pivot point 420 lies on another straight line 421 extending parallel to the longitudinal axis 213 of the cartridge 210, wherein the straight lines 431, 441, 421 all have a different straight-line distance from the longitudinal axis 213 of the cartridge 210. In the embodiment shown, the straight-line distance between the straight line 421 through the pivot point 420 and the longitudinal axis 213 is greatest, followed by the straight-line distance between the straight line 431 through the first form closure 430 and the longitudinal axis 213. The different straight-line distances improve the force distribution of the force required during tilting about the pivot point 420 to open the ampoules 330 onto the two form closures 430, 440, and at the same time allow an optimally space-saving design of the device 100. The latter in particular facilitates the handling of the device 100 by a user.

Figure 3:
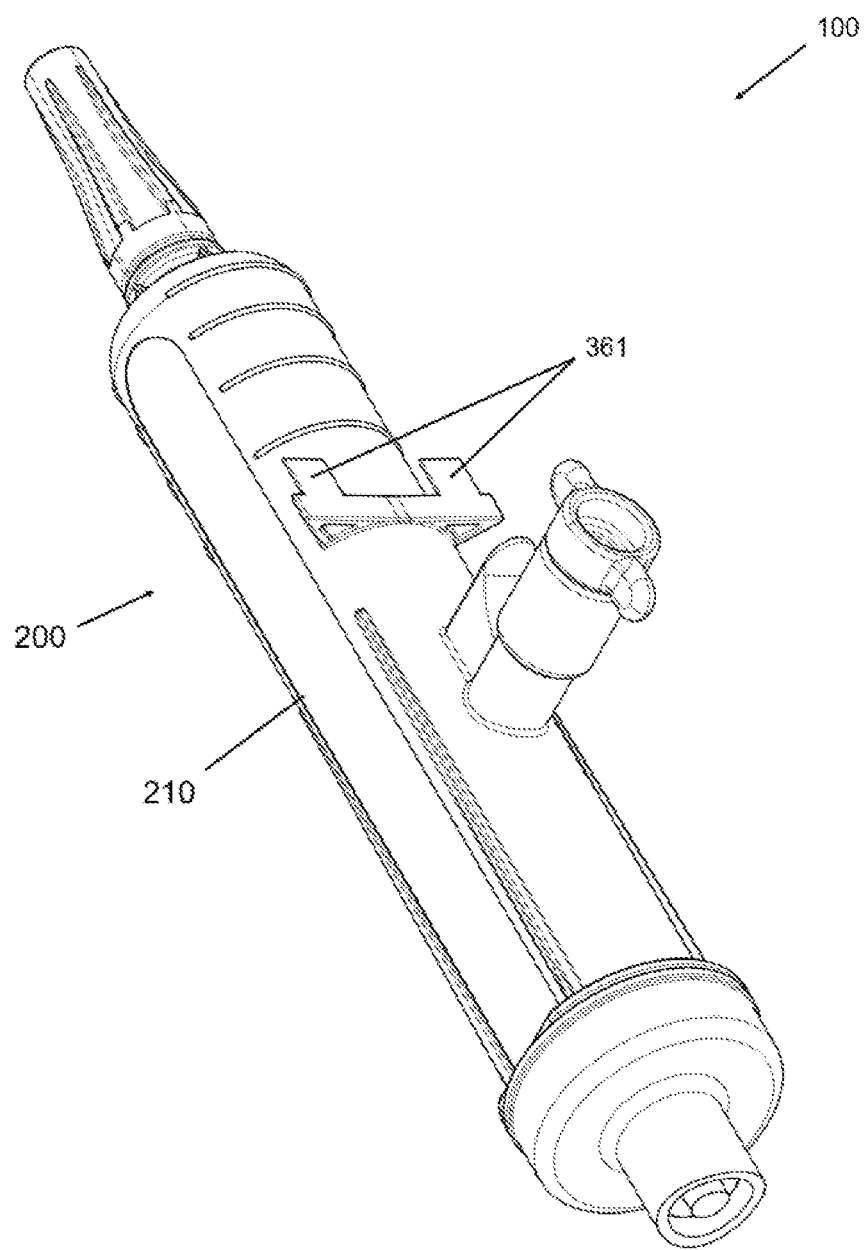

FIG. 3 shows a perspective side view of the mixing unit 200 of the device 100 of FIGS. 1 and 2. The mixing unit 200 comprises two clasp protrusions 261 on an outer surface of the cartridge 210, which are reversibly insertable into clasp indentations on an outer surface of the reservoir 300 (not shown) to form a clasp (not shown) that forms the second form closure (see FIG. 2).

Figure 4:
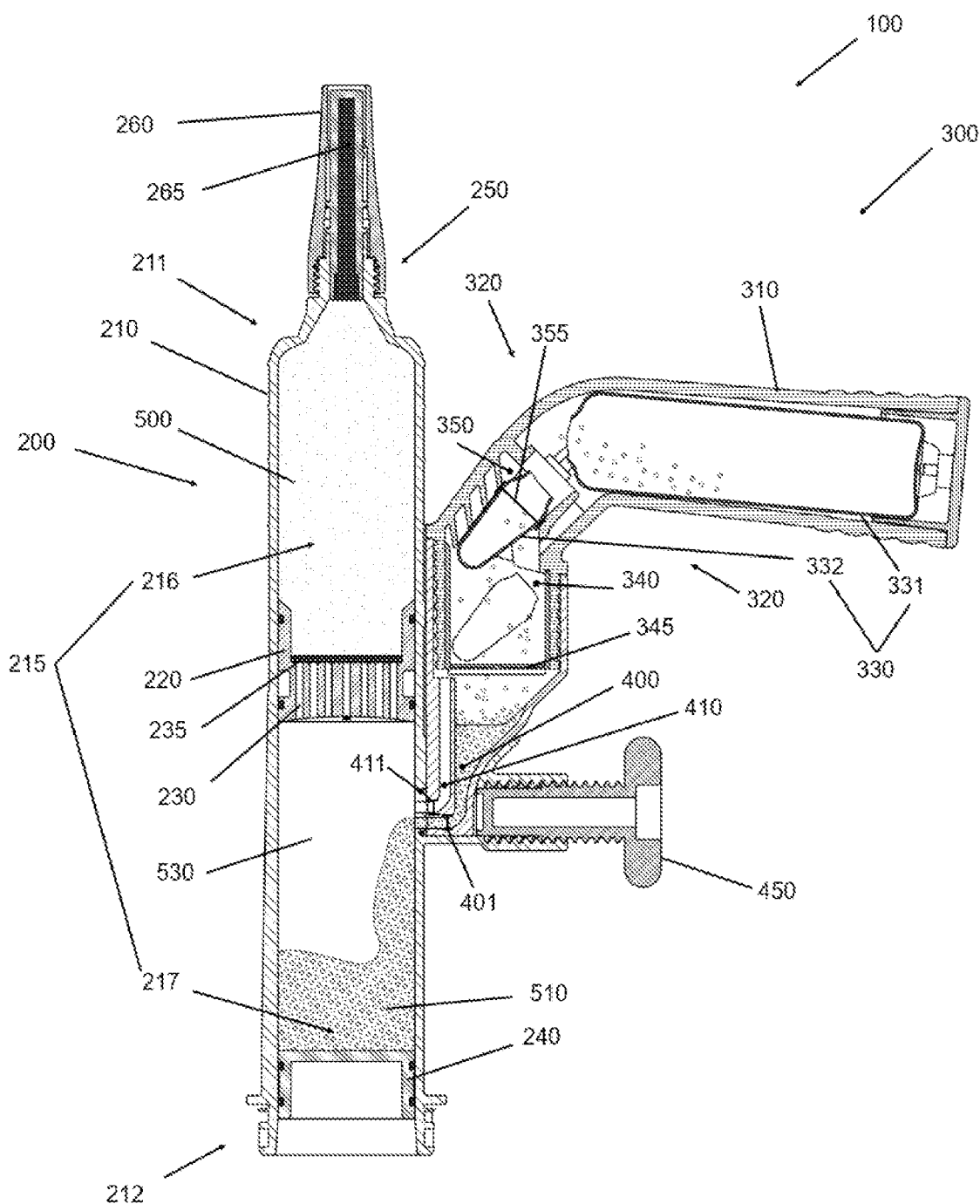

FIG. 4 shows the device 100 of FIGS. 1 to 3 with ampoules 330 tilted about pivot point 420 (see FIG. 2). For this purpose, the reservoir container 310 is bent at the deformable region 320 such that the ampoule heads 332 were pressed against the connection 350 and the ampoules 330 were opened in the region of the ampoule neck 332 (cf. FIG. 1) in a fluid-conducting manner. Most of the monomer liquid 510 stored in the ampoules 330 opened in a fluid-conducting manner has already flowed out of the ampoules 330 via the cavity 340 and the inlet channel 400 into the distal part 217 of the interior space 215. The ampoule head 332 of one of the ampoules 330 has completely transitioned from the connection 350 into the cavity 340. In this case, the ampoule head 332 has been captured by the filter element 345 such that it, or respectively fragments thereof, cannot pass to or through the inlet channel 400. The cavity 340 is dimensioned such that the ampoule head 332 can be mounted so as to be completely rotatable therein, so that monomer liquid 510 that is possibly still present in the ampoule head 332 after the opening of the ampoule 330 can flow out into the cavity 340. This has already happened in FIG. 4. At the same time, a portion of the gas 530 has been discharged from the interior space 215 into the reservoir 300 via the outlet channel 410. The volume of the discharged portion of the gas 530 is substantially equal to the volume of the monomer liquid 510 already introduced into the distal part 217 of the interior space 215.

In order to convey substantially all of the monomer liquid 510 into the mixing unit 200 through the inlet channel 400, rather than through the outlet channel 410, the inlet channel 400 has a smaller distance to the pivot point 420 than the outlet channel 410. Furthermore, the outlet channel 410 opens into the interior space 215 proximal to the inlet channel 400 such that the inflowing monomer liquid 510 does not impede discharge of the gas 530 from the interior space 215 through the outlet channel 410.

Figure 5:
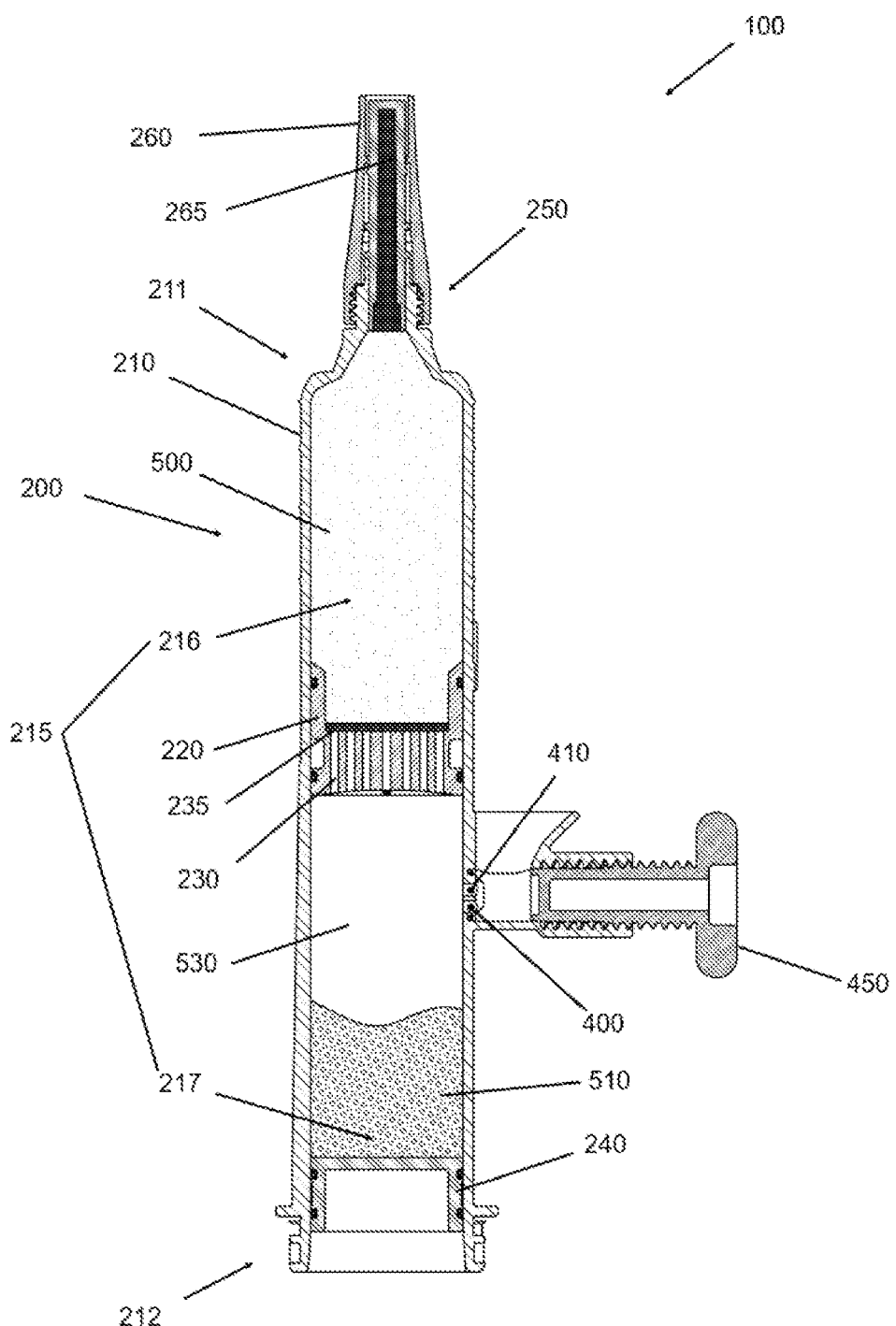

FIG. 5 shows the device 100 of FIGS. 1 to 4, wherein the reservoir 300 has been separated from the mixing unit 200 by releasing the first form closure 430 and the second form closure 440 after substantially complete flow of the monomer liquid 510 into the distal part 217 of the interior space 215. By separating the reservoir 300, the parts of the inlet channel 400 and the outlet channel 410 facing the reservoir 300 were separated in terms of fluid conduction from the parts of the inlet channel 400 and outlet channel 410 facing the mixing unit 200. The inlet channel 400 and the outlet channel 410 are thus in a second channel position separated in terms of fluid conduction.

The distal part 217 of the interior space 215 is connected in a fluid-conducting manner to the surroundings of the device 100 via the part of the inlet channel 400 and outlet channel 410 that faces the mixing unit 200, i.e., the feed-throughs in the cartridge 210. Thus, advancing the conveying piston 240 in the direction of the discharge piston 220 would, in the embodiment of the device 100 shown, discharge the monomer liquid 510 at least partially from the mixing unit 200 instead of, as desired, conveying it substantially completely through the conduit means 230 into the proximal part 216 of the interior space 215 to therein form the bone cement paste together with the bone cement powder 500.

FIG. 6 shows the device 100 of FIGS. 1 to 6, wherein the closure element 450 is screwed in until it contacts the cartridge 210, and thus has been brought into a closure position in which the part of the inlet channel 400 and of the outlet channel 410 that faces the mixing unit 200 is closed off from the surroundings of the device 100 in terms of fluid conduction. In the closure position, the closure element 450 allows substantially complete conveying of the monomer liquid 510 into the proximal part 216 of the interior space by advancing the conveying piston 240 in the direction of the discharge piston 220.

To facilitate conveying of the monomer liquid 510 into the proximal part 216 of the interior space 215 for the user, the distal cartridge end 212 is connected to a discharge aid 550 in the form of a discharge gun that can push distally against the conveying piston 240 to displace it proximally.

Figure 7:
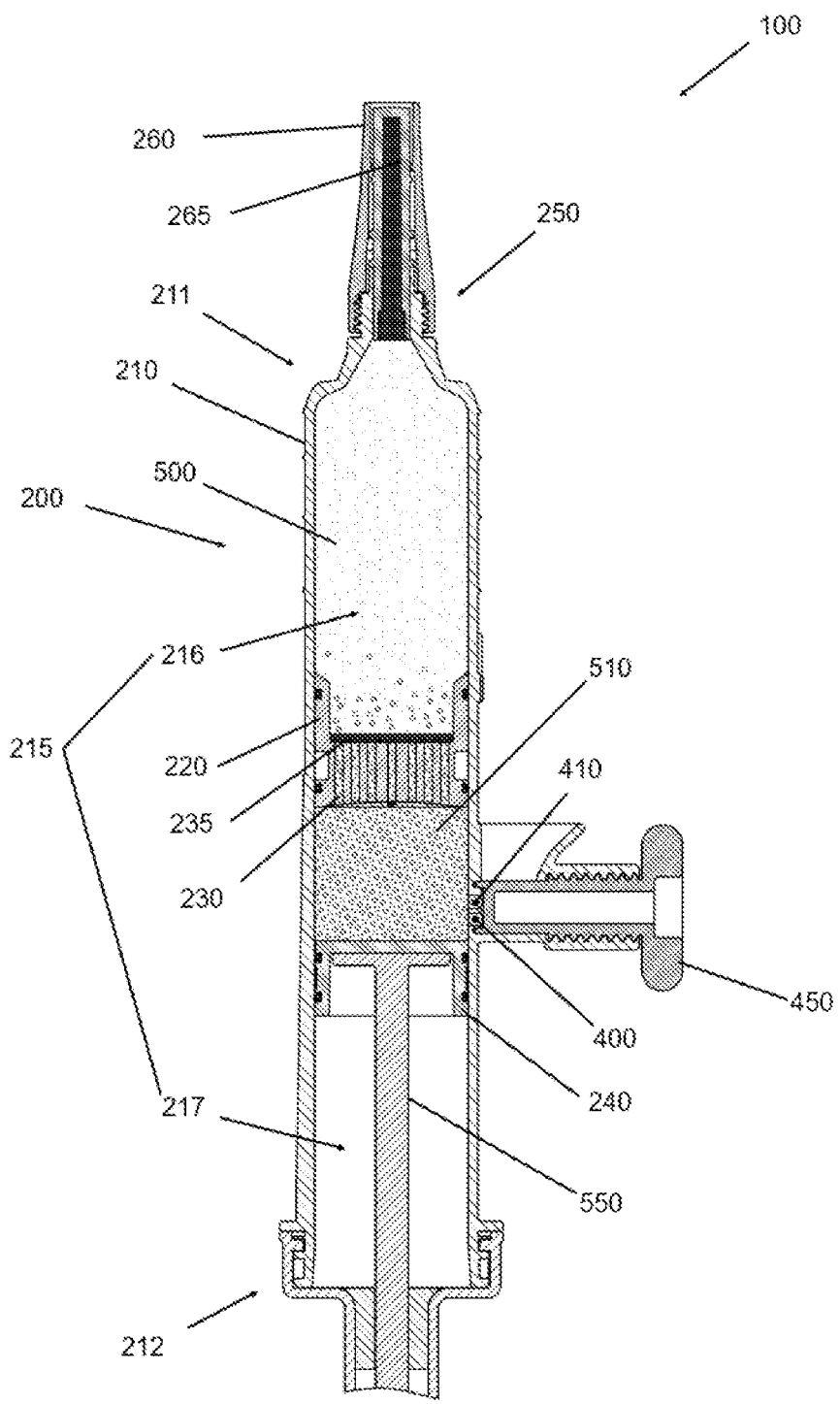

FIG. 7 shows the device 100 of FIGS. 1 to 6 during conveying of the monomer liquid 510 from the distal part 217 of the interior space 215 through the conduit means 230 into the proximal part 216 of the interior space 215. In this regard, due to the sealing means 450 being in the sealing position, no monomer liquid 510 is released from the distal part 217 of the interior space 215 to the surroundings of the device 100.

As the monomer liquid 510 begins to come into contact with the bone cement powder 500, the bone cement paste is formed in the proximal part 216 of the interior space 215. In this context, the hydrophilic additive in the bone cement powder 500 ensures improved distribution of the monomer liquid 510 in the bone cement powder 500, such that provision of a homogeneous bone cement paste is possible without mechanical aids, such as a mixing rod, and thus without mixing equipment.

Figure 8:
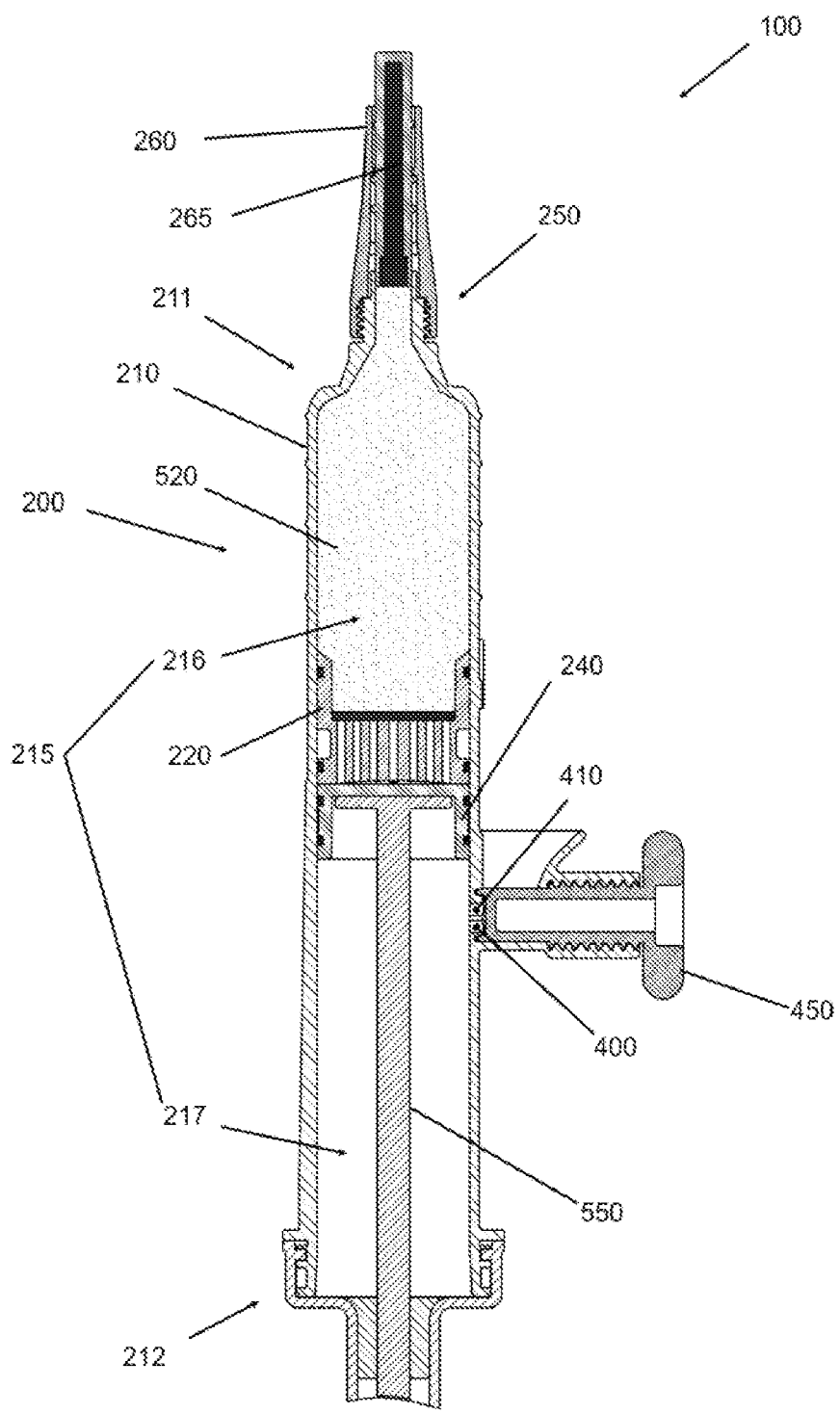

FIG. 8 shows the device 100 of FIGS. 1 to 7 with bone cement paste 520 provided in the proximal part 216 of the interior space 215. For this purpose, the conveying piston 240 was displaced proximally by the discharge aid 550 until it abuts distally against the discharge piston 220. This conveyed substantially all of the monomer liquid 510 into the proximal part 216 of the interior space 215.

The formation of the bone cement paste 520 has resulted in swelling of the bone cement powder 500, which is accompanied by an increase in volume. As a result, the plug 265 has been deployed from the closure cap 260 in portions, signaling to the user of the device 100 that the bone cement paste 520 has been provided.

Figure 9:
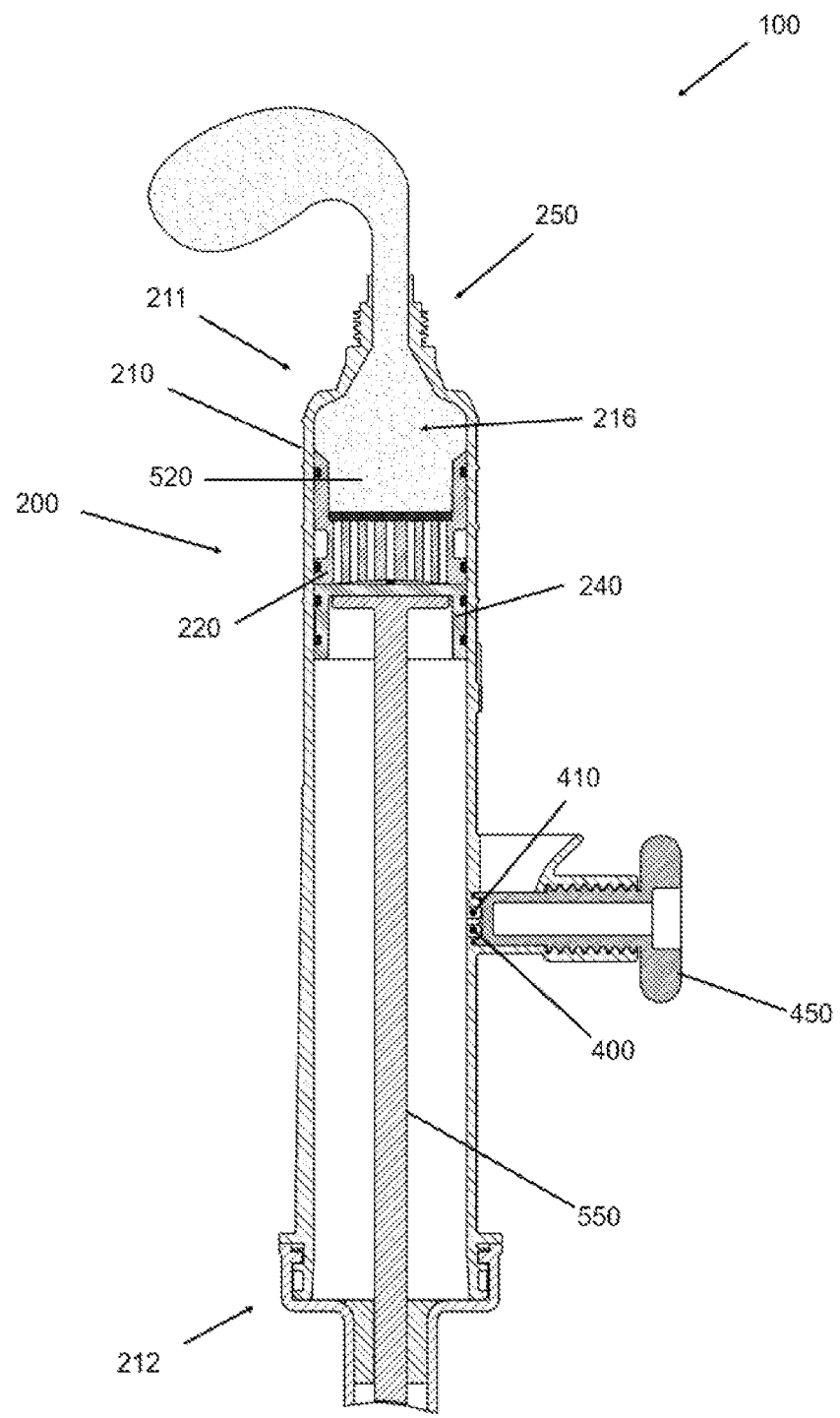

FIG. 9 shows the device 100 of FIGS. 1 to 8 discharging the bone cement paste 520 from the discharge opening 250. For this purpose, the conveying piston 240 together with the discharge piston 220 was advanced in the direction of the discharge opening 550 by a continued advancement of the discharge aid 550. In further embodiments of the device 100 not shown, the discharge opening 250 may be provided with a discharge snorkel to assist in targeted discharge of the bone cement 520.

Figure 10:
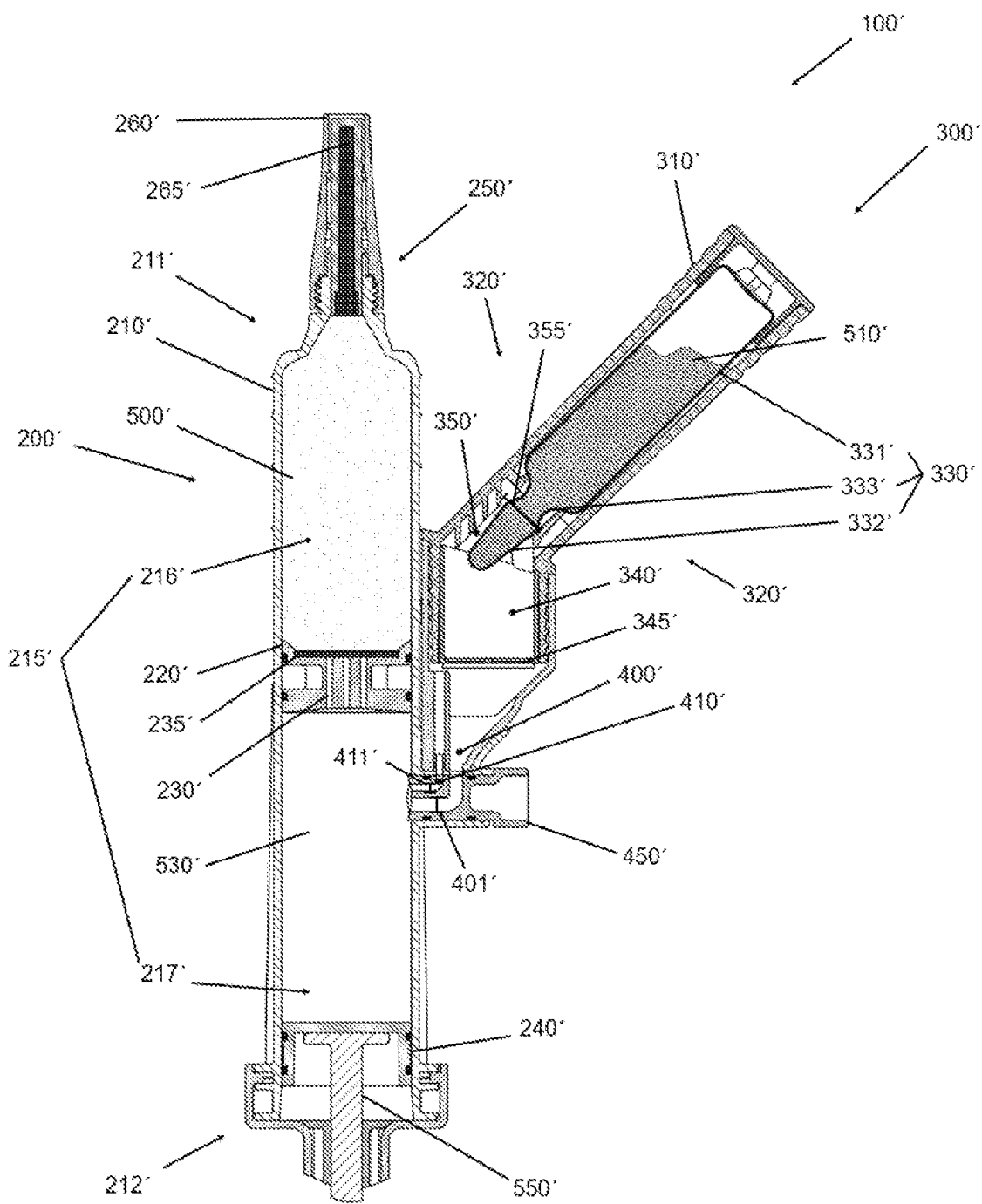

FIG. 10 shows another exemplary embodiment of a device 100' for providing a bone cement paste from two starting components in an initial state. The embodiment of the device 100' largely corresponds to the embodiment described above and shown in FIGS. 1 to 9, and therefore reference is made to the above description in order to avoid repetitions. Modifications of any of the embodiments shown in FIGS. 1 to 9 have the same reference sign with an apostrophe.

The device 100' differs from the device 100 of FIGS. 1 to 9 in that it includes a closure element 450' in the form of a rotary valve. The inlet channel 400' and the outlet channel 410' are designed in two parts, just as in the device 100 of FIGS. 1 to 9, wherein each part of the two channels 400', 410' that faces the mixing unit 200' respectively extends through the closure element 450'. In FIG. 10, the closure element 450' is in a first rotary valve position such that the inlet channel 400' and the outlet channel 410' are in the first channel position connecting the reservoir 300' and the mixing unit 200' to one another in a fluid-conducting manner.

Figure 11:
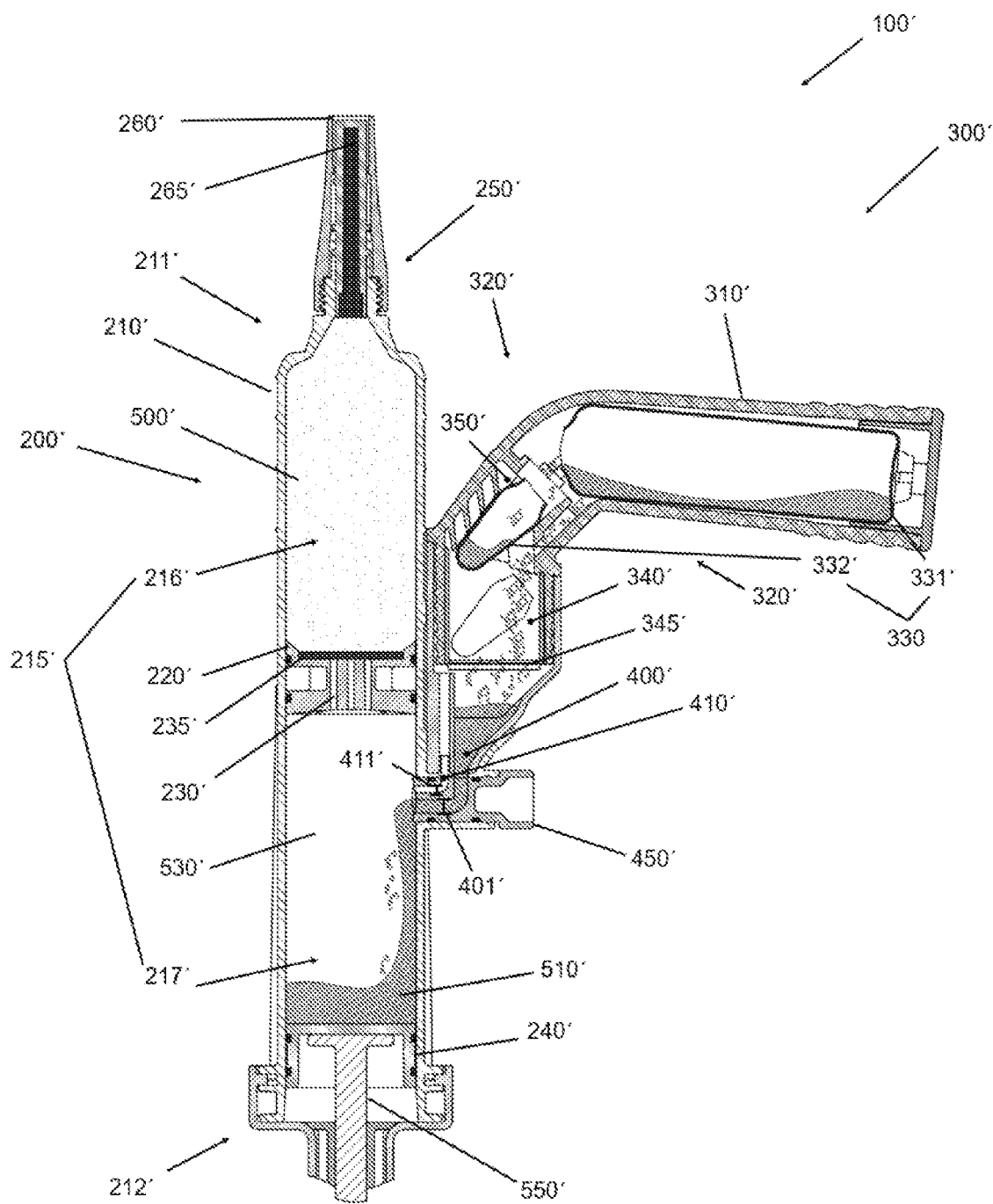

FIG. 11 shows the device 100' of FIG. 10 with ampoules 330' opened in a fluid-conducting manner.

For this purpose, the reservoir container 310' is bent at the deformable region 320' such that the ampoule heads 332' were pressed against the connection 350' and the ampoules 330' were opened in the region of the ampoule neck 332' (cf. FIG. 10) in a fluid-conducting manner. Most of the monomer liquid 510' stored in the ampoules 330' opened in a fluid-conducting manner has already flowed out of the ampoules 330' via the cavity 340' and the inlet channel 400' into the distal part 217' of the interior space 215'. The ampoule head 332' of one of the ampoules 330' has completely transitioned from the connection 350' into the cavity 340'. In this case, the ampoule head 332' has been captured by the filter element 345' such that it, or respectively fragments thereof, cannot pass to or through the inlet channel 400'. The cavity 340' is dimensioned such that the ampoule head 332' can be mounted so as to be completely rotatable therein, so that any monomer liquid 510' that is possibly still present in the ampoule head 332' after the opening of the ampoule 330' can flow out into the cavity 340'. This has already happened in FIG. 11. At the same time, a portion of the gas 530' has been discharged from the interior space 215' into the reservoir 300' via the outlet channel 410'. The volume of the discharged portion of the gas 530' is substantially equal to the volume of the monomer liquid 510' already introduced into the distal part 217' of the interior space 215'.

In order to convey substantially all of the monomer liquid 510' into the mixing unit 200' through the inlet channel 400', rather than through the outlet channel 410', the inlet channel 400' has a smaller distance to the pivot point 420' than the outlet channel 410'. Furthermore, in the first rotary valve position, the outlet channel 410' opens into the interior space 215' proximally to the inlet channel 400' such that the inflowing monomer liquid 510' does not impede discharge of the gas 530' from the interior space 215' through the outlet channel 410'.

Figure 12:
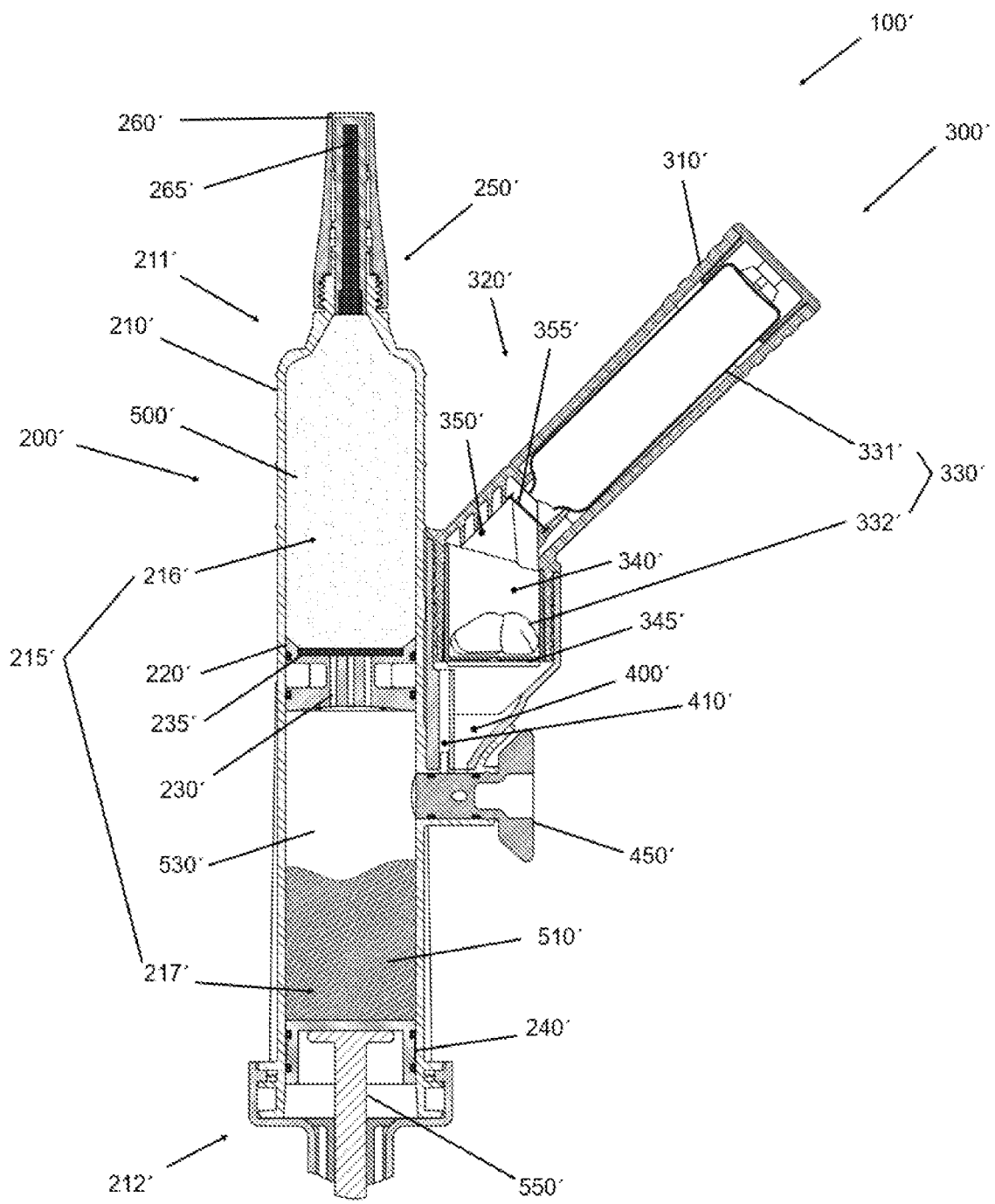

FIG. 12 shows the device 100' of FIGS. 10 and 11 with monomer liquid 510' conveyed substantially completely into the distal part 217' of the interior space 215'. To facilitate substantially complete conveying of the monomer liquid 510' from the distal part 217' of the interior space 215' of the embodiment of the device 100' shown, the closure element 450' in the form of a rotary valve has been brought to a second rotary valve position by a rotation of about an axis of the closure element 450'. The inlet channel 400' and the outlet channel 410' are in a second channel position in the second rotary valve position, in which the mixing unit 200' and the reservoir 300' are separated from one another in terms of fluid conduction. Conveying the monomer liquid 510' into the proximal part 216' of the interior space 215' and providing and discharging the bone cement paste can be performed in a manner analogous to the device 100 as shown in FIGS. 7 to 9.

Figure 13:
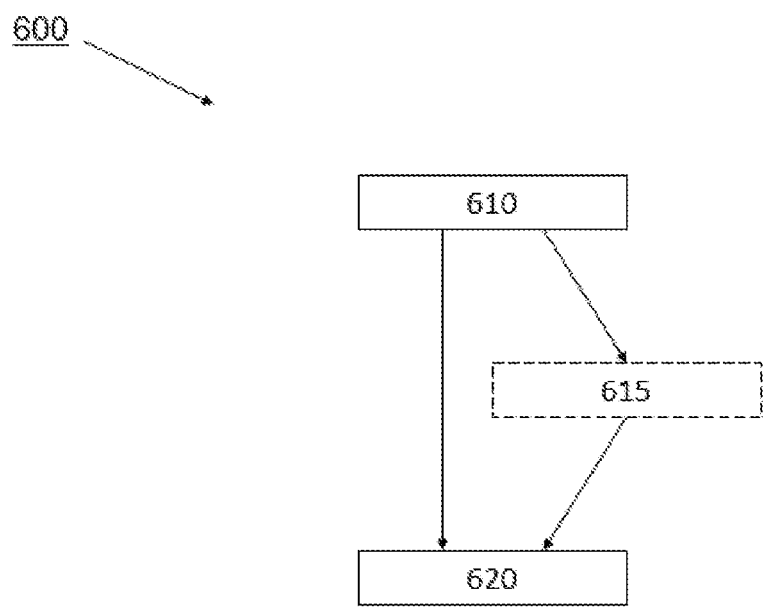

FIG. 13 illustrates a method 600 for providing a bone cement paste 520 from two starting components by means of the devices 100, 100' in accordance with FIGS. 1 to 9 and 10 to 12 comprising steps 610 and 620 and optionally step 615.

In a step 610, the monomer liquid 510, 510' flows from the reservoir 300, 300' through the inlet channel 400, 400' into the distal part 217, 217' of the interior space 215, 215' of the mixing unit 200, 200'. At the same time, the monomer liquid 510, 510' flowing into the distal part 217, 217' of the interior space 215, 215' displaces, according to its volume, the gas 530, 530' present in the interior space 215, 215', which is discharged from the interior space 215, 215' into the reservoir at the same time as the monomer liquid 510, 510' flows in. Thus, the inlet channel 400, 400' synergistically interacts with the outlet channel 410, 410' to improve mass transfer between the reservoir 300, 300' and the mixing unit 200, 200'.

In a step 620, the monomer liquid 510, 510' is conveyed from the distal part 217, 217' of the interior space 215, 215' through the conduit means 230, 230' into the proximal part 216, 216' of the interior space 215, 215'. For this purpose, the conveying piston 240, 240' is advanced in the direction of the discharge piston 220, 220' within the interior space 215, 215'. In order to convey the monomer liquid 510, 510' substantially completely into the proximal part 216, 216' of the interior space 215, 215', the conveying piston 240, 240' is preferably advanced in the direction of the discharge piston 220, 220' until it is in distal contact with the discharge piston 220, 220'.

In a preferred embodiment of the method 600, in a step 615, which takes place between step 610 and step 620, the part of the two-part inlet channel 400, 400' and the two-part outlet channel 410, 410' that faces the mixing unit 200, 200' is closed in terms of fluid conduction by the closure element 450, 450'. This facilitates a substantially complete conveying 620 of the monomer liquid 510, 510' into the proximal part 216, 216' of the interior space 215, 215' because the monomer liquid 510, 510' is not inadvertently discharged, by advancing the conveying piston 240, 240', from the corresponding parts of the channels 400, 400', 410, 410' of the device 100, 100'.

Preferably, prior to step 620, the reservoir 300, 300' is separated from the mixing unit 200, 200' by releasing the first form closure 430 and the second form closure 440, which improves the handling of the device for a user.

When conveying 620 the monomer liquid 510, 510' into the proximal part 216, 216' of the interior space 215, 215', formation of the bone cement paste 520 from the bone cement powder 500, 500' and the monomer liquid 510, 510' occurs. Preferably, the formation of the bone cement paste 520 occurs without mechanical action by the user of the device 100, 100'. The method 600 is thus preferably carried out without mechanical action, for example without actuation of a mixing device, such as a mixing rod.

After the bone cement paste 520 has been provided, it is preferably discharged from the device 100, 100', in particular from the proximal part 216, 216' of the interior space 215, 215', by a continued advancement of the conveying piston 240, 240' in the direction of the discharge opening 250, 250'. In the process, the conveying piston 240, 240' acts from a distal direction on the discharge piston 220, 220', which is thereby moved in the direction of the discharge opening 250, 250'. Conveying 620 of the monomer liquid 510, 510' and discharging of the bone cement paste 520 is thus preferably carried out by means of unidirectional advancement of the conveying piston 240, 240'.

REFERENCE SIGNS 100, 100' device
200, 200' mixing unit
210, 210' hollow cylindrical cartridge
211, 211' proximal cartridge end
212, 212' distal cartridge end
213 longitudinal axis of the cartridge
215, 215' interior space of the cartridge
216, 216' proximal part of the interior space
217, 217' distal part of the interior space
220, 220' discharge piston
230, 230' conduit means
235, 235' filter means
240, 240' conveying piston
250, 250' discharge opening
260, 260' closure cap
265, 265' plug
300, 300' reservoir
310, 310' reservoir container
320, 320' deformable region
330, 330' ampoule
331, 331' ampoule body
332, 332' ampoule head
333, 333' ampoule neck
340, 340' cavity
345, 345' filter element
350, 350' connection
355, 355' connection diameter
361 clasp protrusions
400, 400' inlet channel
401, 401' inlet channel diameter
410, 410' outlet channel
411, 411' outlet channel diameter
420 pivot point
421 straight line through the pivot point
430 first form closure
431 straight line through the first form closure
440 second form closure
441 straight line through the second form closure
450, 450' closure element
500, 500' bone cement powder
510, 510' monomer liquid
520 bone cement paste
530, 530' gas
550, 550' discharge aid
600 method
610 flowing
615 closing
620 conveying

What is claimed is:

1. A device for providing a bone cement paste from two starting components, comprising
a mixing unit comprising a hollow cylindrical cartridge with an interior space, wherein a discharge piston axially movable in the interior space is arranged in the interior space, which discharge piston divides the interior space into a proximal part of the interior space and a distal part of the interior space, wherein the proximal part and the distal part of the interior space are connected to one another in a fluid-conducting manner via a conduit means,
wherein a bone cement powder is stored in the proximal part of the interior space as a first starting component and wherein a conveying piston axially movable in the interior space is arranged in the distal part of the interior space,
and a reservoir for a monomer liquid serving as a second starting component, which is connected or connectable in a fluid-conducting manner via an inlet channel to the distal part of the interior space for introducing the monomer liquid from the reservoir into the mixing unit, wherein
the reservoir and the mixing unit are connected or connectable in a fluid-conducting manner via an outlet channel, via which a gas is discharged from the interior space into the reservoir.

2. The device according to claim 1, wherein the reservoir comprises a reservoir container in which at least one ampoule, closed in terms of fluid conduction, having an ampoule body and an ampoule head is arranged, and the monomer liquid is stored in the at least one ampoule, and comprises a cavity in the region of the ampoule head,
wherein the cavity is connected to the inlet channel in a fluid-conducting manner and comprises a connection to the at least one ampoule, wherein the ampoule head is at least in regions disposed in the connection and the reservoir container comprises, at least in portions, a deformable region such that tilting of the at least one ampoule about a pivot point against the connection is enabled.

3. The device according to claim 2, wherein the inlet channel has a smaller distance to the pivot point than the outlet channel.

4. The device according to claim 1, wherein the outlet channel opens into the interior space proximally to the inlet channel.

5. The device according to claim 1, wherein the inlet channel is designed as a funnel at an inlet channel end opposite the mixing unit.

6. The device according to claim 1, wherein the outlet channel has a minimum outlet channel diameter corresponding to at least half a minimum inlet channel diameter of the inlet channel.

7. The device according to claim 1, wherein the inlet channel and the outlet channel are formed at least in two parts, such that the mixing unit and the reservoir are connected to one another in a fluid-conducting manner in a first channel position of the inlet channel and the outlet channel and are separated from one another in terms of fluid conduction in a second channel position of the inlet channel and the outlet channel.

8. The device according to claim 7, wherein the device comprises a closure element that closes or makes closable, in terms of fluid conduction, at least a part of the two-part inlet channel and the two-part outlet channel that faces the mixing unit.

9. The device according to claim 8, wherein the mixing unit and the reservoir are reversibly connected or connectable to one another via a first form closure.

10. The device according to claim 8, wherein the closure element is a rotary valve, through which the part of the two-part inlet channel and the two-part outlet channel that faces the mixing unit extends and which, in a first rotary valve position, leaves the inlet channel and the outlet channel in the first channel position and, by rotating to a second rotary valve position, moves the inlet channel and the outlet channel to the second channel position.

11. The device according to claim 9, wherein, after the reservoir has been separated from the mixing unit by releasing the first form closure, the closure element is movable into a closure position in order to close, in terms of fluid conduction, the part of the two-part inlet channel and the two-part outlet channel that faces the mixing unit.

12. The device according to claim 11, wherein the closure element is a screw.

13. The device according to claim 9, wherein the mixing unit and the reservoir are reversibly connected or connectable to each other via a second form closure.

14. A method for providing a bone cement paste from two starting components using the device of claim 1, the method comprising:
   a. flowing the monomer liquid from the reservoir through the inlet channel into the distal part of the interior space while simultaneously discharging a gas from the interior space through the outlet channel into the reservoir,
   b. conveying the monomer liquid from the distal part of the interior space through the conduit means into the proximal part of the interior space by means of advancing the conveying piston in the direction of the discharge piston.

15. The method according to claim 14, wherein, prior to conveying the monomer liquid in step b., the part of the two-part inlet channel and the two-part outlet channel that faces the mixing unit is closed in terms of fluid conduction by the closure element.

* * * * *